United States Patent
Lee et al.

(10) Patent No.: US 7,150,879 B1
(45) Date of Patent: *Dec. 19, 2006

(54) NEUTRAL SELF-SETTING CALCIUM PHOSPHATE PASTE

(75) Inventors: Dosuk D. Lee, Brookline, MA (US); Christian Rey, Castanet (FR); Maria Aiolova, Brookline, MA (US); Aliassghar Tofighi, Belmont, MA (US)

(73) Assignee: Etex Corporation, Cambridge, MA (US)

( * ) Notice: Subject to any disclaimer, the term of this patent is extended or adjusted under 35 U.S.C. 154(b) by 1151 days.

This patent is subject to a terminal disclaimer.

(21) Appl. No.: 09/569,081

(22) Filed: May 11, 2000

Related U.S. Application Data

(63) Continuation of application No. 08/729,344, filed on Oct. 16, 1996, which is a continuation-in-part of application No. 08/650,764, filed on May 20, 1996, which is a continuation-in-part of application No. 08/446,182, filed on May 19, 1995, now Pat. No. 5,676,976.

(51) Int. Cl.
*A61F 13/00* (2006.01)

(52) U.S. Cl. .................. 424/422; 106/690; 106/691; 423/308; 423/311; 424/484; 424/601; 424/602; 424/606; 523/113; 523/115; 523/116; 524/414; 524/436; 623/16

(58) Field of Classification Search ................ 106/690, 106/691; 623/16; 423/308, 311; 523/113, 523/115, 116; 524/414, 436; 424/601, 602, 424/606, 484, 422
See application file for complete search history.

(56) References Cited

U.S. PATENT DOCUMENTS

| | | | |
|---|---|---|---|
| 4,157,378 A | 6/1979 | Tomlinson et al. |
| 4,429,691 A | 2/1984 | Niwa et al. |
| 4,612,053 A | 9/1986 | Brown et al. |
| 4,684,673 A | 8/1987 | Adachi |

(Continued)

FOREIGN PATENT DOCUMENTS

| EP | 0 268 463 | 5/1988 |
|---|---|---|

(Continued)

OTHER PUBLICATIONS

Abboudi et al., "Development of Organic and Polymer Carriers for Demineralized Bone Matrix: Effect on Bone Cell Behavior" *Fifth World Congress*, Toronto, Canada (May 29-Jun. 2, 1996).

(Continued)

*Primary Examiner*—Neil S. Levy
(74) *Attorney, Agent, or Firm*—Clark & Elbing LLP

(57) ABSTRACT

The present invention provides a novel process for producing a calcium phosphate cement or filler which hardens in a temperature dependent fashion in association with an endothermic reaction. In the reaction a limited amount of water is mixed with dry calcium phosphate precursors to produce a hydrated precursor paste. Hardening of the paste occurs rapidly at body temperature an is accompanied by the conversion of one or more of the reactants to poorly crystalline apatitic calcium phosphate. The hardened cements, fillers, growth matrices, orthopedic and delivery devices of the invention are rapidly resorbable and stimulate hard tissue growth and healing.

12 Claims, 21 Drawing Sheets

U.S. PATENT DOCUMENTS

| | | | |
|---|---|---|---|
| 4,737,411 | A | 4/1988 | Graves, Jr. et al. |
| 4,849,193 | A | 7/1989 | Palmer et al. |
| 4,880,610 | A | 11/1989 | Constantz |
| RE33,161 | E | 2/1990 | Brown et al. |
| 4,917,702 | A | 4/1990 | Scheicher et al. |
| RE33,221 | E | 5/1990 | Brown et al. |
| 4,938,938 | A | 7/1990 | Ewers et al. |
| 4,959,104 | A | 9/1990 | Iino et al. |
| 5,034,059 | A | 7/1991 | Constantz |
| 5,037,639 | A | 8/1991 | Tung |
| 5,047,031 | A | 9/1991 | Constantz |
| 5,053,212 | A | 10/1991 | Constantz et al. |
| 5,085,861 | A | 2/1992 | Gerhart et al. |
| 5,129,905 | A | 7/1992 | Constantz |
| 5,149,368 | A | 9/1992 | Liu et al. |
| 5,152,836 | A | 10/1992 | Hirano et al. |
| 5,164,187 | A | 11/1992 | Constantz et al. |
| 5,178,845 | A | 1/1993 | Constantz et al. |
| 5,262,166 | A | 11/1993 | Liu et al. |
| 5,279,831 | A | 1/1994 | Constantz et al. |
| 5,281,265 | A | 1/1994 | Liu |
| 5,286,763 | A | 2/1994 | Gerhart et al. |
| 5,336,264 | A | 8/1994 | Constanz et al. |
| 5,342,441 | A | 8/1994 | Mandai et al. |
| 5,352,715 | A | 10/1994 | Wallace et al. |
| 5,427,754 | A | 6/1995 | Nagata et al. |
| 5,470,803 | A | 11/1995 | Bonfield et al. |
| 5,496,399 | A | 3/1996 | Ison et al. |
| 5,501,706 | A | 3/1996 | Arenberg |
| 5,516,532 | A | 5/1996 | Atala et al. |
| 5,522,893 | A | 6/1996 | Chow et al. |
| 5,525,148 | A | 6/1996 | Chow et al. |
| 5,542,973 | A | 8/1996 | Chow et al. |
| 5,545,254 | A | 8/1996 | Chow et al. |
| 5,562,895 | A | 10/1996 | Tung |
| 5,565,502 | A | 10/1996 | Glimcher et al. |
| 5,605,713 | A | 2/1997 | Boltong |
| 5,626,861 | A | 5/1997 | Laurencin et al. |
| 5,665,120 | A | 9/1997 | Ohtsuka et al. |
| 5,683,461 | A | 11/1997 | Lee et al. |
| 5,691,397 | A | 11/1997 | Glimcher et al. |
| 5,770,289 | A | 6/1998 | Breitbert et al. |
| 5,782,971 | A * | 7/1998 | Constantz et al. .......... 106/690 |
| 5,846,312 | A | 12/1998 | Ison et al. |
| 6,005,162 | A * | 12/1999 | Constantz .................... 623/16 |
| 6,201,039 | B1 * | 3/2001 | Brown et al. ................ 523/115 |

FOREIGN PATENT DOCUMENTS

| | | |
|---|---|---|
| EP | 0 347 028 | 4/1989 |
| EP | 0 664 133 | 2/1994 |
| JP | 63-111875 | 5/1988 |
| JP | 63-170205 | 7/1988 |
| JP | 2-182261 | 7/1990 |
| JP | 5-305134 | 11/1993 |
| JP | 06228011 | 12/1994 |
| JP | 7277712 | 10/1995 |
| WO | 90/00892 * | 2/1990 |
| WO | 92/001009 | 1/1992 |
| WO | 92/02453 | 2/1992 |
| WO | 94/04657 | 8/1993 |
| WO | 94/20064 | 9/1994 |
| WO | 95/08319 | 9/1994 |
| WO | 94/02412 | 7/1995 |
| WO | 96/36562 | 5/1996 |
| WO | 97/17285 | 11/1996 |

OTHER PUBLICATIONS

Aoki, "Science and Medical Applications of Hydroxy apatite" *JAAS* pp. 11-15 (1991).

Appel et al., "Recent Advances in Implants for Bone Growth Promotion" *Exp. Opin. Ther. Patents* 4:1461 (1994).

Athanasou et al., "Current Concepts Review: Cellular Biology of Bone-Resorbing Cells" *J. Bone and Joint Surg.* 78A:1096-1112 (1996).

Attawia et al., "The Long Term Osteoblast Response to Poly (anhydride-co-imides): A New Degradable Polymer for Use in Bond" *Fifth World Congress*, Toronto, Canada (May 29-Jun. 2, 1996).

Barton et al., "Surface and Bulk Properties of Amorphous Calcium Phosphate" *Colloid Interface Sci* [Proc. Int. Conf.] $50^{th}$ 3:71 (1976 [CA 87:73954v] (Abstract).

Besic et al., "Electron Probe Microanalysis of Noncarious Enamel and Dentin and Calcified Tissue in Mottled Teeth" *J. Dent. Res.* 48:131 (1969).

Blumenthal et al., "Effect of Preparation Conditions on the Properties and Transformation of Amorphous Calcium Phosphate" *Mt. Res. Bull.* 7:1181 (Nov. 1972).

Boskey, "Matrix Proteins and Mineralization: An Overview" *Connect. Tiss. Res.* 35:357-363 (1996).

Constantz et al., "Skeletal Repair by in Situ Formation of the Mineral Phase of Bone" *Science* 267:1976 (1995).

Denissen et al., "Net-shaped Hydroxy apatite Implants for Release of Agents Modulating Periodontal-like Tissues" *J. Periodontal Res.* 32:40-46 (1997).

Driessens et al., "Calcium Phosphate Bone Cements" *Encyc. Hand. Biomet. And Bioeng.* 855-877 (1994).

Eanes et al., "Intermediate States in the Precipitation of Hydroxy apatite" *Nature* 208:365-367 (1965).

Eanes et al., "Intermediate Phases in the Basic Solution Preparation of Alkaline Earth Phosphates" *Calcified Tissue Res.* 2:38 (1968) [CA 69:110373f](Abstract).

Eanes et al., "Thermochemical Studies on Amorphous Calcium Phosphate" *Calc. Tiss. Res.* 5:133 (1970).

Fukase, "Setting Reactions and Compressive Strengths of Calcium Phosphate Cements" *J. Dent. Res.* 69:1852 (Dec. 1990).

Gao, "Established Competence of Bioactive Composite Bone Substitute on the Healing of Diaphseal Segmental Defects in Sheep" *Fifth World Congress*, Toronto, Canada (May 29-Jun. 2, 1996).

Glimcher et al., "Recent Studies of the Mineral Phase in Bone and its Possible Linkage to the Organic Matrix by Protein-Bound Phosphate Bonds" *Phil. Trans. R. Soc. Lond. B* 304:479-508 (1984).

Glimcher et al., "Recent Studies of Bone Mineral: Is the Amorphous Calcium Phosphate Theory Valid" *Jour. Of Crystal Growth* 53:100-119 (1981).

Graves et al., "Resorbable Ceramic Implants" *J. Biomed. Mater. Res.* 324:55 (1996).

Greenfield et al., "Formation Chemistry of Amorphous Calcium Phosphates Prepared from Carbonate Containing Solutions" *Cal. Tiss. Res.*, 9:152 (1972).

Hayes et al., "Augmentation of Cementless Femoral Stems to Improve Initial Stability Using a Remodelable Calcium-Phosphate Bone Mineral Substitute" $61^{st}$ *Annual American Academy of Orthopedic Surgeons Meeting*, New Orleans (Feb. 1994).

Hirasawa et al., "Manufacture of High Purity Hydroxyapatite," *Chemical Abstracts*, 108(10):166 No. 78193h (Mar. 7, 1988).

Hollinger et al., "Role of Substitutes" *Clin. Ortho. & Related Res.* 324:55 (1996).

Holmes et al., "Surface Areas by Gas Adsorption on Amorphous Calcium Phosphate and Crystalline Hydroxyapatite" *Calc. Tiss. Res.* 7:163 (1971).

Horioglu et al., "Long Term Follow-up of Hydroxyapatite Cement (HAC) Implants for Craniofacial Reconstruction" $21^{st}$ *Annual Meeting of the Society of Biomaterials* (Mar. 18-22, 1995).

Hubell, "Biomaterials in Tissue Engineering" *Bio/Technology* 13:56 (1995).

Ishikawa et al., "Effects of Preparation in Aqueous Solution on Properties of Hydroxyapatites" *Dent. Mater. J.* 9(1):58 (1990) [CA 113:218168j](Abstract).

Kim et al., "Hyaluronan-based Biodegradable Scaffolds for Skeletal Tissue Reconstruction" *Fifth World Congress*, Toronto, Canada (May 29-Jun. 2, 1996).

Kinoshita et al., "Reconstruction of Mandibular Discontinuity Defects in Dogs Using Autogenic Particular Cancellous Bone and Marrow and Poly(L-lactide) Mesh" *Fifth World Congress*, Toronto, Canada (May 29-Jun. 2, 1996).

Labarthe et al., "Sur la Structure et les Properiétié s des Apatites Carbonateés de Type B Phospho-Calciques" *Ann. Chem.* 8:289 (1973).

Norian "The Material Science of Norian SRS, Skeletal Repair System" (available to applicant Fall, 1997).

Nylen et al., "Molecular and Ultrastructural Studies of Non-Crystalline Calcium Phosphates" *Calc. Tiss. Res.* 9:95 (1972).

Oka et al., "Development of Artificial Osteochondral Composition Material" *Fifth World Congress*, Toronto, Canada (May 29-Jun. 2, 1996).

Otsuka et al., "Effect of Particle Size of Metastable Calcium Phosphates on Mechanical Strength of a Novel Self-setting Bioactive Calcium Phosphate" *J. Biomed. Mat. Res.* 29:25 (1995).

Pool, "Coral Chemistry Leads to Human Bone Repair" Science 269:1772 (Mar. 1995).

Posner et al., "Synthetic Amorphous Calcium Phosphate and Its Relation to Bone Mineral Structure" *Bone Mineral Structure* 8:273-281 (1975).

Rey et al., "Preparation of Microporous Ceramic at Low Temperature from Poorly Crystalline Apatite" *Symposium Abstract* (1993).

Rey et al., "The Carbonate Environment in Bone Mineral: A Resolution-enhanced Fourier Transform Infrared Spectroscopy Study" *Calcif. Tissue Int.*, 45:157 (1989).

Rey et al., Chemical Properties of Poorly Crystalline Apatites *Phosphorus Res. Bull.* 6:67-70 (1996) (Abstract).

Rizkalla et al., "Effect of Composition on Strength of Bioactive Composites" *Fifth World Congress*, Toronto, Canada (May 29-Jun. 2, 1996.)

Selmani et al., "Bioerodible Polyester Foams for Orthopaedic Tissue Culture" *Fifth World Congress*, Toronto, Canada (May 29-Jun. 2, 1996).

Shindo et al., "Facial Skeletal Augmentation Using Hydroxy apatite Cement" *Arch. Otolaryngol Head Neck Surg.* vol. 119 (Feb. 1993).

Termine et al., "Amorphous/Crystalline Interrelationships in Bone Mineral" *Calc. Tiss. Res.* 1:8-23 (1967).

Thissen et al., "Surface Modification of Bioresorbable Polymers by Plasma Induced Graft Polymerization" *Fifth World Congress*, Toronto, Canada (May 29-Jun. 2, 1996).

Törmälä, "Biodegradable Self-Reinforced Composite Materials; Manufacturing Structure and Mechanical Properties" *Clin. Mat.* 10:29 (1992).

Tung et al., "An Intermediate State in Hydrolysis of Amorphous Calcium Phosphate" *Calcif. Tissue Int.* 35:783 (1983).

Yasue et al., "Effect of Adsorption of Succinic Acid on the Formation of Amorphous Calcium Phosphate" *J. Ceram. Soc.* Japan 102(12):1 (Dec. 1994).

* cited by examiner

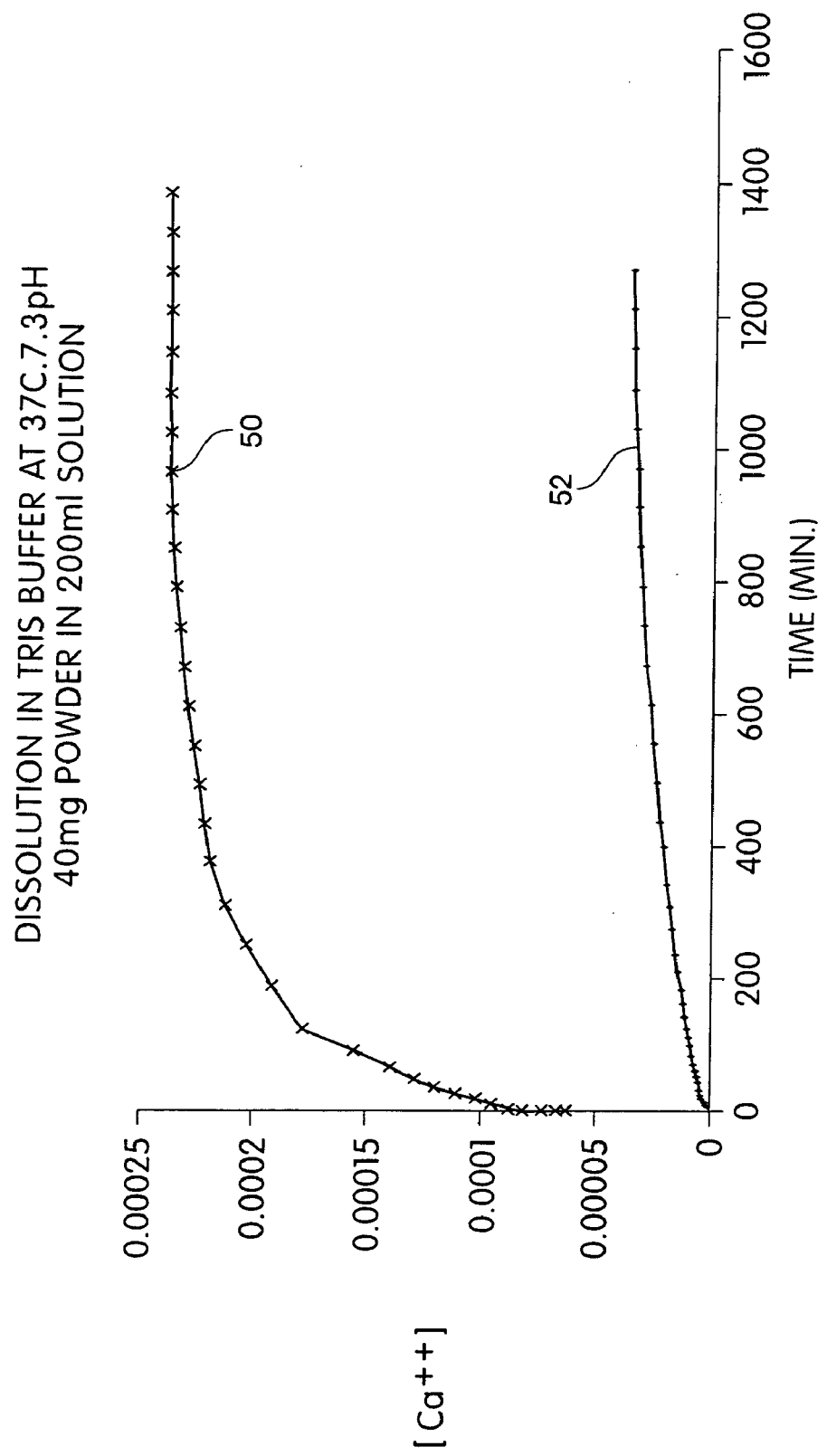

NEUTRAL SELF-SETTING CALCIUM PHOSPHATE PASTE

This application is a continuation application of co-pending application U.S. Ser. No. 08/729,344 filed Oct. 16, 1996 entitled "Methods and Products Related to the Physical Conversion of Reactive Amorphous Calcium Phosphate", which is a continuation-in-part application of co-pending application U.S. Ser. No. 08/650,764 filed May 20, 1996 entitled "Novel Bone Substitution Material and a Method of Its Manufacture", which is a continuation-in-part application of application U.S. Ser. No. 08/446,182 filed May 19, 1995 now U.S. Pat. No. 5,676,976 entitled "Synthesis of Reactive Amorphous Calcium Phosphates", all of which are herein incorporated in its entirety by reference. This application also is related to several co-pending applications filed on even day herewith entitled, "Bioresorbable Ceramic Composites", U.S. Ser. No. 08/732,016, now issued as U.S. Pat. No. 6,027,742 "Delivery Vehicle", U.S. Ser. No. 08/729,342 "Cell Seeding of Ceramic Compositions" U.S. Ser. No. 08/729,354 and "Orthopedic and Dental Ceramic Implants", U.S. Ser. No. 08/729,343 each of which is incorporated by reference.

FIELD OF THE INVENTION

This invention relates to hard tissue implant materials containing poorly crystalline apatitic calcium phosphate useful as human or animal implantable bioceramics and for other purposes. The invention further relates to bioresorbable composites, cell therapy and therapeutic substance delivery devices useful in human and animal therapeutics.

BACKGROUND OF THE INVENTION

Calcium phosphates are the principal constituent of hard tissues (bone, cartilage, tooth enamel and dentine). Calcium phosphates generally occur in apatitic form when found in biological tissues. For instance, the composition of bone mineral may be represented by the following formula:

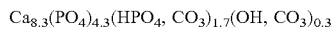

$Ca_{8.3}(PO_4)_{4.3}(HPO_4, CO_3)_{1.7}(OH, CO_3)_{0.3}$

Unlike the ideal stoichiometric crystalline hydroxyapatite $(Ca_{10}(PO_4)_6(OH)_2)$, or stoichiometric apatites in general $(Ca_5(PO_4)_3X)$, which have a calcium to phosphate ratio (Ca/P) of 1.67, bone mineral is a non-stoichiometric apatite. Its non-stoichiometry is primarily due to the presence of divalent ions, such as $CO_3^{2-}$ and $HPO_4^{2-}$, which are substituted for the trivalent $PO_4^{3-}$, ions. Substitution by $HPO_4^{2-}$ and $CO_3^{2-}$ ions produces a change of the Ca/P ratio, resulting in Ca/P ratio which may vary between 1.50 to 1.70, depending on the age and bony site. Generally, the Ca/P ratio increases during aging of bone, suggesting that the amount of carbonate species increases for older bones. Naturally-occurring bone mineral is made of nanometer-sized, poorly-crystalline calcium phosphate with apatitic structure. The poorly crystalline apatitic calcium phosphate of bone is distinguished from the more crystalline hydroxyapatites and non-stoichiometric hydroxyapatites by its distinctive XRD pattern as shown in FIG. 7. It is the Ca/P ratio in conjunction with nanocrystalline size and the poorly-crystalline nature that yields the specific solubility properties of the bone minerals. And because bone tissues undergo constant tissue repair regulated by mineral-resorbing cells (Osteoclasts) and mineral-producing cells (Osteoblasts), solubility behavior of minerals is important in maintaining a delicate metabolic balance between these cell activities.

Synthetic bone graft material made to closely resemble natural bone minerals can be a useful replacement for natural bone. Acceptable synthetic bone can avoid the problem of availability and harvesting of autologous bone (patient's own bone) and the risks and complications associated with allograft bone (bone from a cadaver), such as risks of viral transmission. An ideal synthetic bone graft should possess a minimum of the following four properties: (1) it should be chemically biocompatible; (2) it should provide some degree of structural integrity in order to keep the graft in place and intact until the patient's own bone heals around it; (3) it should be resorbable so that the patient's own bone ultimately replaces the graft; and, (4) because it may be necessary to incorporate cells and/or biomolecules into the synthetic bone material, it is desirable that the process used to form the material employ low temperatures and chemically mild conditions. Similar criteria are also important for other hard tissue grafts (e.g. cartilage).

These criteria may be met by a material in which parameters, such as Ca/P ratios, crystal size, crystallinity, porosity, density, thermal stability and material purity are controlled. While there have been considerable efforts to synthesize a ceramic material for use as implants, synthetic hydroxyapatites have most often been used because their chemical formulae are very similar to the naturally occurring mineral in bone. LeGeros R. Z., in Calcium Phosphates in Oral Biology and Medicine, Karger Pub. Co., New York, 1991 teaches highly crystalline forms of hydroxyapatite produced by solution precipitation followed by sintering at high temperatures (800–1200° C.). High temperature treatment yields highly stoichiometric hydroxyapatite with crystal sizes on the order of several microns with a Ca/P of 1.67. Such highly crystalline hydroxyapatite is essentially non-resorbable in vivo. It is not replaced by living bone tissue and remains intact in the patient for an undesirably extended period of time.

A number of other approaches to the production of bone substitute material have employed hydroxyapatite produced by a solid-state acid-base reaction of primarily crystalline calcium phosphate reactants. These hydroxyapatite bone substitute materials are sometimes poorly-reacted, inhomogeneous, and have significant crystalline hydroxyapatite content.

Constantz in U.S. Pat. No. 4,880,610 reports on the preparation of calcium phosphate minerals by the reaction of a highly concentrated phosphoric acid with a calcium source in the presence of a base and hydroxyapatite crystals. The resultant product is a polycrystalline material containing a crystalline form of hydroxyapatite minerals. Likewise, U.S. Pat. No. 5,053,212 to Constantz et al. discloses the use of a powdered acid source to improve the workability and mixability of the acid/base mixture; however, a mixed-phase calcium phosphate material similar to that of U.S. Pat. No. 4,880,610 is reported. Recently, Constantz et al. reported in Science (Vol. 267, pp. 1796–9 (24 Mar., 1995)) the formation of a carbonated apatite from the reaction of monocalcium phosphate monohydrate, Beta-tricalcium phosphate, Alpha-tricalcium phosphate, and calcium carbonate in a sodium phosphate solution, to provide a calcium phosphate material which is still substantially more crystalline in character than naturally occurring bone minerals.

Similarly, Brown et al. in U.S. Reissue No. 33,221 report on the reaction of crystalline tetracalcium phosphate (Ca/P of 2.0) with acidic calcium phosphates. Liu et al. in U.S. Pat. No. 5,149,368 disclose the reaction of crystalline calcium phosphate salts with an acidic citrate.

A number of calcium phosphate bone fillers and cements have been described as "resorbable." Generally, these are compounds comprising or derived from tricalcium phosphate, tetracalcium phosphate or hydroxyapatite. At best these materials may be considered only weakly resorbable. Of these, the tricalcium phosphate compounds have been demonstrated to be the most resorbable and after many years of study they are still not widely used in clinical settings. The tricalcium phosphates are known to have lengthy and somewhat unpredictable resorption profiles, generally requiring in excess of one year for resorption. Furthermore, unless steps are taken to produce extremely porous or channeled samples, the tricalcium phosphates are not replaced by bone. Recently it has been concluded that the "biodegradation of TCP, which is higher than that of Hap [hydroxyapatite] is not sufficient" (Berger et al., Biomaterials, 16:1241 (1995)). Tetracalcium phosphate and hydroxyapatite derived compounds are also only weakly resorbable. Tetracalcium phosphate fillers generally exhibit partial resorption over long periods of time such as 80% resorption after 30 months (Horioglu et al., Soc. for Biomaterials, Mar. 18–22, pg 198 (1995)). Approximately 30% of microcrystalline hydroxyapatite implanted into the frontal sinus remained after 18 months in cats.

All of these references disclose a chemical reaction resulting in crystalline form of hydroxyapatite solids that has been obtained by reacting crystalline solids of calcium phosphate. There has been little reported on the use of amorphous calcium phosphates (Ca/P of approximately 1.5) as one of the reactants because the amorphous calcium phosphates are the least understood solids among the calcium phosphates and amorphous calcium phosphate has traditionally been considered to be a relatively inert and non-reactive solid.

Amorphous calcium phosphate material has been used as a direct precursor to the formation of a highly crystalline hydroxyapatite compounds under generally high temperature treatments. Such a highly crystalline material is inappropriate for synthetic bone because it is highly insoluble under physiological conditions. Chow et al. in U.S. Pat. No. 5,525,148 report the testing of ACP precursors in a number of reaction schemes but states that slurries of a variety of crystalline calcium phosphates including ACP either alone or in mixtures do not produce a setting cement or act as an effective remineralizing agent.

Brown et al. in U.S. Reissue No. 33,221 report on the formation of crystalline hydroxyapatite for dental cement by reacting an amorphous phase specifically restricted to tetracalcium phosphate (Ca/P of 2.0) with at least one of the more acidic calcium phosphates. Further, Brown et al., does not disclose the preparation or the properties of such a tetracalcium phosphate in amorphous state. Tung in U.S. Pat. No. 5,037,639 discloses the use and application of standard amorphous calcium phosphate paste for the remineralization of teeth. Tung proposes the use of standard inert amorphous calcium phosphate mixed with and delivered through a chewing gum, mouth rinse or toothpaste, which upon entering oral fluids converts to crystalline fluoride containing hydroxyapatite which is useful to remineralize tooth enamel. Simkiss in PCT/GB93/01519 describes the use of inhibitors, such as Mg ions or pyrophosphate, mixed with amorphous calcium phosphate and implanted into living tissues. Upon leaching of, for example Mg ions, into surrounding bodily fluids, the amorphous calcium-magnesium phosphate converts into a more crystalline form.

There remains a need to develop new synthetic materials that more closely mimic the properties of naturally-occurring minerals in hard tissue. In particular, there remains a need to provide synthetic bone materials which are completely bioresorbable, which can be formed at low temperatures and are poorly-crystalline, with nanometer-sized crystals.

SUMMARY OF THE INVENTION

The present invention provides a bioactive ceramic material that is biocompatible, bioresorbable and workable for long period of time at room temperature. The bioactive ceramic material may be formed at low temperatures, is readily formable and/or injectable, and yet can harden to high strength upon further reaction. The bioactive ceramic material contains poorly crystalline apatitic calcium phosphate solids with Ca/P ratios comparable to naturally occurring bone minerals and having stiffness and fracture toughness similar to natural bone. The bioactive ceramic composite material is strongly bioresorbable and its biosorbability and reactivity can be adjusted to meet the demands of the particular therapy and/or implant site. The material may be prepared as bone plates, bone screws and other fixtures and medical devices, including veterinarian applications, which are strongly bioresorbable and/or ossifying.

These and other features of the invention are accomplished by a self-hardening bioceramic composition, including a hydrated precursor of a calcium phosphate and an aqueous-based liquid in an amount sufficient to hydrate the calcium phosphate to form a paste or putty, characterized in that hardening of the hydrated precursor is associated with an endothermic reaction. Alternatively, a self-hardening bioceramic composition, includes a hydrated precursor of an amorphous calcium phosphate and an aqueous-based liquid in an amount sufficient to hydrate the calcium phosphate to form a paste or putty, characterized in that hardening of the hydrated precursor occurs in more than ten minutes.

In another aspect of the invention, a bioceramic composition is provided including a poorly crystalline calcium phosphate prepared by promoting the hardening of a hydrated precursor comprising an amorphous calcium phosphate and an aqueous-based liquid in an amount sufficient to hydrate the amorphous calcium phosphate to form a paste or putty, whereby hardening is associated with an endothermic reaction and the conversion of the amorphous calcium phosphate into the poorly crystalline calcium phosphate.

The bioceramic composition of the invention may be prepared by mixing in any order, (a) an amorphous calcium phosphate, (b) a promoter, and (c) an aqueous-based liquid in an amount sufficient to form a paste or putty, whereby the paste or putty is converted into a poorly crystalline apatitic calcium phosphate and said conversion is associated with hardening of the paste in an endothermic reaction.

DEFINITIONS

"Amorphous"—By "amorphous" as that term is used here, it is meant a material with significant amorphous character. Significant amorphous character contemplates greater than 75% amorphous content, preferably greater than 90% amorphous content, and is characterized by a broad, featureless X-ray diffraction pattern. It is recognized that a small degree of crystallinity may exist in the material. However, for the amorphous precursor materials of the present invention, it is preferable that the degree of crystallinity be less than that desired in the product material.

"Bioactive"—"Bioactive" refers to a material that induces hard tissue formation in and about the implant. When implanted in soft tissue, the bioactivity may also require the presence of a growth or trophic factor, or the seeding of the implant with a hard tissue forming cell type.

"Biocompatible"—The term "biocompatible", as used herein, means that the material does not elicit a substantial detrimental response in the host. There is always concern, when a foreign object is introduced into a living body, that the object will induce an immune reaction, such as an inflammatory response that will have negative effects on the host. For example, although hydroxyapatite is generally considered to be "biocompatible", significant inflammation and tissue necrosis have been observed when crystalline hydroxyapatite microcarriers are inserted intramuscularly in animals (see, for example, IJntema et al., *Int. J. Pharm* 112:215 (1994).

"Bioresorbable"—"Bioresorbable" refers to the ability of a material to be resorbed in vivo. "Full" resorption means that no significant extracellular fragments remain. The resorption process involves elimination of the original implant materials through the action of body fluids, enzymes or cells. Resorbed calcium phosphate may, for example, be redeposited as bone mineral, or by being otherwise reutilized within the body, or excreted. "Strongly bioresorbable", as that term is used herein, means that at least 80% of the total mass of material implanted intramuscularly or subcutaneously is resorbed within one ear. In preferred embodiments of the invention, the poorly crystalline apatitic (PCA) phosphate is characterized in that, when at least 1 g (preferably 1–5 g) of PCA material is implanted at a subcutaneous or intramuscular site, at least 80% of the material is resorbed within one year. In more preferred embodiments, the material will be resorbed within nine months, six months, three months, and ideally one month. Furthermore, particularly preferred materials are characterized in that they can be fully resorbed in the stated time periods. For the purpose of this disclosure, "weakly" resorbable means that less than 80% of the starting material is resorbed after one year.

"Hardening"—"Hardening" refers to the process by which the hydrated precursor is transformed into a hardened PCA material. The PCA material is considered to be "hardened" when it is a substantially non-formable solid. Such a hardened PCA material has minimal compressibility and tends to undergo plastic as opposed to elastic deformation.

"Hydrated precursor"—The term "hydrated precursor", as used herein, refers to the paste or putty formed by hydration of the dry precursors in the presence of a limited amount of aqueous solution (i.e., less than approximately 1 mL aqueous solution/1 g precursor powder). The hydrated precursor may comprise both reactants and products, in various combinations, depending on the extent to which the conversion has progressed. Both the "injectable" and "formable" precursor pastes described herein are hydrated precursors. Preferred "injectable" hydrated precursors have a consistency appropriate for delivery through an 18 gauge needle.

"Poorly crystalline apatitic calcium phosphate", "PCA calcium phosphate" and "PCA material", as those terms are used herein, describe a synthetic poorly crystalline apatitic calcium phosphate. The PCA material is not necessarily restricted to a single calcium phosphate phase provided it has the characteristic XRD and FTIR pattern. A PCA calcium phosphate has substantially the same X-ray diffraction spectrum as bone. The spectrum is generally characterized by only two broad peaks in the region of 20–35° with one centered at 26° and the other centered at 32°. It is further characterized by FTIR peaks at 563 $cm^{-1}$, 1034 $cm^{-1}$, 1638 $cm^{-1}$ and 3432 $cm^{-1}$ (±2 $cm^{-1}$). Sharp shoulders are observed at 603 $cm^{-1}$ and 875 $cm^{-1}$, with a doublet having maxima at 1422 $cm^{-1}$ and 1457 $cm^{-1}$.

"Promoter"—The term "promoter", as used herein, describes a material or treatment that promotes hardening of a hydrated precursor and may enhance the ACP to PCA calcium phosphate conversion. Some promoters participate in the conversion and are incorporated into the product PCA material; others, known as "passive" promoters, do not participate.

"Reactive"—"Reactive" is used herein to refer to the ability of an amorphous calcium phosphate when mixed with liquid to form a hydrated precursor to undergo conversion to the PCA material of the present invention in the presence of a promoter in association with hardening of the precursor materials. Preferred ACPs are characterized by an ability to convert completely, an ability to convert quickly with hardening, an ability to undergo conversion with otherwise inert compounds and/or an ability to convert into a substantially homogeneous PCA material. Where the ACP is reacted with a second calcium phosphate, the "conversion" can encompass conversion of both the ACP and the second calcium phosphate. The degree of hardening and the kinetics of the hardening process are also important elements of reactivity. Some ACPs are more reactive than others. An ACP is considered "highly reactive" if it undergoes conversion and hardening to a PCA material in the presence of a weak promoter, such as dicalcium phosphate dihydrate ("DCPD") with a grain size distribution containing a significant fraction of grains greater than 100 μm. Preferred highly reactive ACPs produce a hardened PCA material in the presence of weakly promoting DCPD and water at 37° C. in less than twelve hours, with hardening being substantially complete in about one to five hours, and ideally 10–30 minutes.

BRIEF DESCRIPTION OF THE DRAWING

FIG. 3 is a solubility curve of a poorly crystalline apatitic calcium phosphate product derived from amorphous calcium phosphate of the present invention, as compared with a crystalline hydroxyapatite. Note the relative higher solubility of the material of the present invention versus a more crystalline form of hydroxyapatite, as measured by the amount of calcium ions released into solution at 37° C.;

FIG. 9 presents photomicrographs of tibial defects either untreated (9a) or treated (9b) with a PCA material of the present invention.

DETAILED DESCRIPTION OF THE INVENTION

Figure 1:
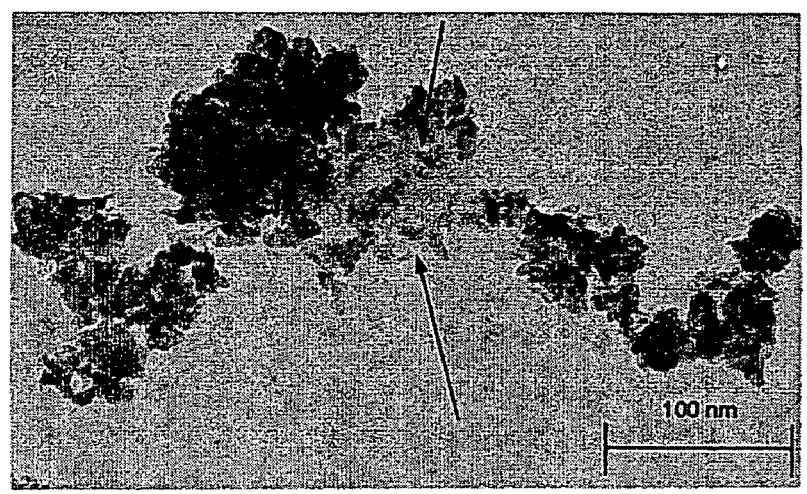
FIG. 1 is a high-resolution transmission electron micrograph of the reactive amorphous calcium phosphate illustrating the nanometer-sized grains in clusters with relatively unclear boundaries and partially immersed in shapeless form (arrows)

The present invention is directed to biocompatible ceramic compositions adapted for use in the repair and growth promotion of hard tissue including the fabrication of resorbable orthopedic and dental fixtures. The compositions comprise a biocompatible and highly bioresorbable poorly crystalline apatitic calcium phosphate (PCA calcium phosphate) sometimes combined with a suitable biocompatible matrix or additive. The PCA calcium phosphate has utility in dental, orthopedic, drug delivery, cell therapy and other therapeutic applications.

The inventive composition may be applied as a bone cement to the bone-contacting surfaces of prosthetic devices. It may be applied directly to bone defects as a filler, where it is capable of promoting the growth of new bone tissue. The composition may similarly be applied for repair, growth or production of cartilaginous tissue. Alternatively, the composition may be used to fabricate fixtures or devices such as screws and plates, which under appropriate circumstances will be resorbed and replaced by bone or cartilage. The composition may also be used free standing in soft tissue. When a pharmaceutically active agent is added to the composition, it serves as a drug delivery device, and release of the agent may occur over an extended time period after implantation as the composition slowly biodegrades.

The invention also provides methods for promoting the conversion of ACP to PCA calcium phosphate, in a controlled fashion, in the form of a paste or putty which hardens predictably.

The PCA calcium phosphate bioceramic of the invention is generally calcium deficient with a calcium to phosphate ratio of less than 1.5 as compared to the ideal stoichiometric value of approximately 1.67 for hydroxyapatite. They are further characterized by their biological bioresorbability and minimal crystallinity. They may be rapidly bioresorbable and possess high porosity and/or low density or slowly bioresorbable and possess decreased porosity and/or high density. Their crystalline character is substantially the same as natural bone without the higher degree of crystallinity seen in the bone substitute materials known to the art. The inventive PCA calcium phosphate also is biocompatible, that is, there is no significant detrimental reaction (e.g., inflammation or fibrosis) induced in the host by the implanted material. Materials which induce a medically acceptable level of inflammation or fibrosis are considered biocompatible. The PCA calcium phosphate may be used in a moist precursor form (i.e., hydrated precursor) and applied as a cement directly to a surgical site such as a fracture, or it may be hardened ex vivo and subsequently implanted.

The resorbability of the inventive PCA calcium phosphate is attributable to a combination of density, porosity, chemical composition and crystalline structure. Low crystallinity in apatites is associated with somewhat increased solubility in aqueous systems compared to other more crystalline species, and thus the low crystallinity and/or presence of stable amorphous apatitic domains in the inventive PCA calcium phosphate is believed to be associated with its resorbability in biological systems. Porosity facilitates both the penetration of cells and cell processes into the bioceramic matrix and the diffusion of substances to and from the matrix interior. Accordingly, PCA calcium phosphate compositions of lower porosity resorb more slowly in vivo than those of high porosity. In one embodiment, the use of controlled particle size reactants leads to a PCA calcium phosphate material of controlled porosity. Other methods of promoting porosity may be employed, such as chemical or physical etching and leaching.

The inventive PCA calcium phosphates may be manufactured with a variety of resorption rates ranging from slow resorption times of greater than one year (typical of weakly resorbing hydroxyapatites bone fillers and bone substitutes known to the art) to resorption rates as fast as several grams, e.g., 1–5 g, in 1 to 2 months. Thus depending upon the density, porosity, reactants used, final crystallinity of the reaction product, and the amount of crystallization inhibitors used, formulations can be prepared in which a one gram device will fully resorb in any desired time period—from 2 weeks to 1, 3 or 6 months to 1, 2 or three years. A strongly resorbable PCA calcium phosphate of the instant invention possesses an in vivo resorption rate in which 80% or more of at least one gram preferably 1–5 g) of starting material is resorbed within one year, preferably within 6 months, more preferably in less than 3 months, and most preferable within 1–2 months.

For the production of new bone in load bearing situations it has been found that preparations which are fully resorbed and replaced by bone in about six to eight weeks lead to histologically normal bone by 12 weeks. In some load bearing situations it may be desirable to have resorption occur more slowly. Additionally, when hard tissue is being prepared ectopically or the shape of an existing hard tissue is to be augmented, it may be desirable to employ more slowly resorbing PCA calcium phosphate.

Adjustment of the density or porosity of the resultant PCA calcium phosphate or the use of reaction parameters which affect the speed and hardness of setting are all useful approaches to varying the in vivo resorption time of the inventive PCA calcium phosphate. These parameters may be adjusted alone or in combination as required by specific applications.

Slow resorption (greater than three months) is favored by the use of high density, low porosity PCA calcium phosphate and/or rapid reaction and hardening times. Fast resorption (three or less months) is favored by the use of low density, high porosity PCA calcium phosphate, and/or slow reaction and setting times. Guidance for adjustment of rate and completeness of reaction to form the PCA calcium phosphate are given elsewhere herein. The following describes the production of preferred PCA calcium phosphate precursors which lead to a hardened PCA calcium phosphate cements of differing resorbability kinetics in vivo.

A rapidly resorbing PCA calcium phosphate is obtained by conversion of the highly reactive ACP of Example 5 using a DCPD with a grain size distribution having a considerable content of grain sizes greater that 100 μm (e.g. corresponding to distribution B1 in Table 3) as a promoter. The powders are prepared as a hydrated precursor as described in Example 8.

A slowly resorbing PCA calcium phosphate is obtained by conversion of the highly reactive ACP of Example 5 using DCPD with a grain size distribution having a minimal content of grain sizes greater than 100 μm (e.g. corresponding to distribution B3 in Table 3) as a promoter. The powders are prepared as a hydrated precursor as described in Example 9.

The inventive PCA calcium phosphate undergoes ossification. Ossification refers to the replacement of the implanted synthetic calcium phosphate with bone which histologically is similar or identical to natural bone. Ossification of the inventive PCA calcium phosphate tends to occur in stages with more unorganized bone appearing prior to the establishment of more natural appearing tissue. The inventive PCA calcium phosphate is different from previous bone fillers and cements because bone formation does not occur only at the outer edge of the implant, but initiates simultaneously throughout the implant, presumably in association with the resorptive process. Within two to three weeks following implantation of the PCA material into a load bearing region, such as the tibia or radius, preliminary ossification is observed by the formation of small foci of mineralized osteoid formation (spicules). By four weeks, the spicules have given way to lacy appearing thin cancellous trabecular bone and thin cortical bone. At six weeks, ordered normal or thicker than normal compact cortical bone with lacunae-containing osteocytes is observed. At time points after six weeks, final remodelling occurs so that by twelve weeks the newly ossified bone is indistinguishable from native bone.

Thus, ossification in the presence of PCA calcium phosphate generally reaches completion and appears to occur more rapidly than normal bone growth. This rapid rate of ossification suggests the inventive PCA calcium phosphate enhances bone healing. New bone is observed as early as two weeks and may reach the fully histologically organized state within six weeks, but in any case by 3–6 months. In sheep segmental defect fracture models employing implants of up to 3 gms of hydrated precursor, bone having 100% of the strength of non-fractured bone was found within three months. In the presence of trophic or growth factors such as bone morphogenic proteins this process may be accelerated.

In preferred embodiments, in order to optimize ossification, devices, pastes and putties of the invention may be seeded with bone forming cells. This is most easily accomplished by placing the device (containing PCA calcium phosphate or a hydrated precursor thereto) in contact with a source of the patient's own bone forming cells. Such cells may be found in bone-associated blood or fluids, including exogenous fluids which have been in contact with bone or bone materials or regions, including the periosteum, cortical bone, cancellous bone or marrow. They are also present in tissue including cortical or cancellous bone, bone marrow or periosteum. In the case of devices such as screws and pins, the introduction of which into bone is accompanied by bleeding, no further seeding is required. For plates, which oppose only cortical bone, induction of a periosteal lesion which will contact the device is recommended. In yet other embodiments, it will be useful to surgically prepare a seating within the bone by removing a portion of cortical bone at the implant site. Other steps may also be taken to augment ossification, including introduction of bone forming cells harvested from the patient into the graft, or incorporation of trophic factors or bone growth inducing proteins into, or onto the device. Non-autologous bone cells are also within the scope of the invention if the desired amount of bone regeneration occurs prior to host rejection of the bone forming cells. Thus, cells or tissues obtained from primary sources, cell lines or cell banks may all be useful in certain embodiments. Similar considerations apply for cartilage formation and healing and the seeding of the inventive PCA calcium phosphate with chondrocytes and/or other cartilage forming cells.

Due to the nature of the reaction used to produce preferred formulations of the inventive PCA calcium phosphate, the ease of use as an implant material in a surgical setting is significantly improved over other bone substitute materials known to the art. Specifically, the reaction is initiated outside the body and proceeds slowly at room temperature thereby minimizing the possibility that the material will "set up" and become unusable prior to application to the surgical site. The reaction accelerates significantly at body temperature and the material hardens in place. Furthermore, the consistency and formability of the inventive PCA calcium phosphate as well as the reaction speed may be varied according to the therapeutic need, by modifying a few simple parameters.

Preparation of a PCA Calcium Phosphate. Many amorphous calcium phosphates tend to spontaneously convert to a more crystalline form over time. Hydroxyapatite is a thermodynamically favored form of calcium phosphate and is often the product of such conversion. The instant invention has recognized the value of a controlled conversion of an ACP to a more crystalline form (e.g. PCA calcium phosphate) without significant further crystallization, particularly when the conversion is performed in the presence of a limited amount of water and is accompanied by a hardening reaction. The instant invention provides reactions which lead to the formation of PCA calcium phosphate. These reactions advantageously may be initiated outside of the body, using a precursor having a paste or putty consistency and may be significantly accelerated at 37° C. leading to a hardened calcium phosphate product. In some embodiments, the hardened PCA calcium phosphate alone has a durometer and bulk modulus similar to traditional blackboard chalk. In some instances, hardened PCA material will be associated with the presence of unreacted precursors, promoters, and/or supplemental materials, side products and by-products.

According to the method of the invention, a paste- or putty-like hydrated precursor is formed by addition of water to a calcium phosphate precursor. The hydrated precursor is then heated to about 37° C., thereby initiating a substantially net endothermic reaction which is characterized by hardening of the paste or putty, as indicated by the differential scanning calorimeter (DSC) data shown in FIG. 16. In preferred embodiments, the PCA calcium phosphate material is produced from a hydrated precursor by conversion of a reactive amorphous calcium phosphate to PCA calcium phosphate in the presence of a promoter. Promoting the conversion of ACP in a paste form to well crystallized hydroxyapatite, accompanied by hardening of the paste via an endothermic reaction is also considered to be within the scope of the invention An endothermically setting bone cement provides several important advantages over calcium phosphate bone cements and fillers known in the art. Because the reaction does not give off heat there is no danger of heat related damage to cells and tissues in the implant area. Additionally, the endothermic nature of the reaction means reaction progress can be controlled by regulating the amount of heat available to support the reaction. The hydrated precursor reacts minimally at room temperature and below. This means that many of the handling problems associated with surgical cements and fillers known to the art are avoided.

In preferred embodiments, the reactants are mixed outside of the body, yielding a hydrated PCA calcium phosphate precursor material suitable for application to a surgical site. The reaction generally is completed after application to the surgical site, although in some embodiments the reaction is completed ex vivo. The PCA calcium phosphate reactions of the invention generally lead to hardening of the hydrated precursor in less than five hours, substantially hardening in about one to five hours under physiological conditions, and preferably in about 10–30 minutes. In a preferred embodiment, the reaction is initiated by adding physiological saline to a mixture of two dry components to form a thick paste which hardens in association with an endothermic reaction at 37° C. in about a half an hour. Other aqueous agents such as but not limited to, water, buffer solutions, serum or tissue culture medium may be used in place of Buffers may be used in any pH range, but most often will be used in the range of 5.0 to 8.0. In preferred embodiments, the pH will be compatible with prolonged stability and efficacy of a desired therapeutic agent and, in most preferred embodiments, will be in the range of 5.5 to 7.4. Suitable buffers include, but are not limited to carbonates, and organic buffers such as Tris, HEPES, and MOPS.

Under any reaction scheme it is important that the ACP retains significant amorphous character prior to conversion. Specifically, the overall crystallinity within the starting ACP cannot exceed that desired in the end product. Thus certain reaction schemes may require stabilization of the amorphous nature of the ACP throughout the reaction period. Examples of suitable inhibitors of crystal formation known to the art include carbonate, pyrophosphate, and magnesium. Additional guidance for the use of inhibitors of crystallization may be found in Elliot, Structure and Chemistry of the Apatites and Other Calcium Orthophosphates, Elsevier, The Netherlands, 1994, herein incorporated by reference.

Types of Promoters. The purpose of the promoter is to promote the hardening of the hydrated precursor and preferably to accelerate the conversion of ACP to a PCA calcium phosphate. Any material or method which serves this purpose is considered to be within the scope of the reaction. This includes the limited case where hardening occurs in the absence of conversion, that is when a PCA calcium phosphate precursor is used as the starting material.

With respect to the conversion of ACP, a promoter may promote the overall reaction or any intermediate reactions involved in the conversion or hardening process. In this regard preferred promoters will reduce the activation energy for one or more specific steps in the conversion or hardening process.

The promoter used to convert a reactive ACP to the inventive PCA calcium phosphate may itself be converted to PCA calcium phosphate calcium phosphate or otherwise participate in a chemical or physical reaction during the conversion process. Such promoters are referred to herein as "participating" promoters.

Alternatively a promoter may remain substantially unchanged during the reactive ACP conversion serving essentially to catalyze or to initiate or enhance PCA nucleation and hardening. These promoters are referred to as "passive" promoters.

Promotion of the hardening and conversion of a reactive ACP to PCA calcium phosphate through the use of other means such as the use of heat, pressure, reactive gases, solvents, ionic solutions, or radiochemistry is also considered within the scope of the invention. Such promoting means are termed reaction enhancing or "enhancing" promoters.

Promoters may have different abilities or strengths in the promotion of the production of a hardened PCA calcium phosphate from ACP. Likewise, not all ACPs are equally reactive. Thus weak promoters will not always be effective in reacting with ACPs with low reactivity. In such circumstances stronger promoters will be preferred. Promoter strength may conveniently be tested by comparing the reactivity of a given promoter with the preferred carbonated ACP of the invention in both its heat activated highly reactive form as well as its non heat activated form using the method described in Example 8. The use of hand mixing of reactants is particularly suited for identification of highly reactive promoters. Less reactive promoters may benefit from mixing in an automated mill as described in Example 9. By use of these methods DCPD with the grain size distribution of B1 in example 10 was demonstrated to be a weak promoter, where as grain sizes in the range of <100 μm were found to be strongly reaction promoting.

In addition to the guidance given above for the matching of a particular promoter to a given ACP, such matching may be done empirically by mixing a given ACP with a selected promoter in the presence of about 1.0 mL water/g powder and heating the mixture at 37° C. in a moist environment. A suitable promoter exhibits PCA calcium phosphate formation and paste hardening under these conditions.

The method of preparation of the promoter and/or the ACP will affect the ease by which the hydrated precursor is converted into the PCA material. As noted above, the method of mixing the powdered reactants prior to addition of liquid affects the reactivity of the system. Thus, hand mixing using a mortar and pestle does not result in as reactive a system as a prolonged machine grinding of the reactant powders. Therefore when comparing promoters, it is important to use standardized preparation conditions.

It is hypothesized that the conversion of ACP to the reactive PCA calcium phosphate is a surface catalyzed phenomenon. If so, it may be desirable to produce a particular promoter with a reproducible surface area. Thus, to control reaction reproducibility it is advantageous to provide a promoter with a known grain size distribution. Standard sieving techniques are suitable for selection of specific grain sizes.

Many calcium- or phosphate-containing compounds may be used as participating promoters in the hardening reaction. A calcium phosphate promoter, may be of any crystalline structure and should be chosen so as to be reactive with ACP either directly or through the use of enhancing promoters. Preferred participating promoters are those which tend themselves to undergo conversion to hydroxyapatite through an intermediate PCA calcium phosphate phase.

Appropriate participating calcium phosphate promoters include neutral, basic and acidic calcium phosphates, preferably apatitic phosphates, which provide the appropriate stoichiometry for reaction to obtain an apatitic calcium phosphate. Suitable calcium phosphate promoters include, but are in no way limited to, calcium metaphosphate, dicalcium phosphate dihydrate, monetite, heptacalcium phosphate, tricalcium phosphates, calcium pyrophosphate dihydrate, hydroxyapatite, poorly crystalline apatitic calcium phosphate, tetracalcium phosphate, calcium pyrophosphate, octacalcium phosphate, and a second ACP. Other sources of phosphate or calcium, such as by way of example only, CaO, $CaCO_3$, calcium acetate, and $H_3PO_4$, may be mixed to form a final product to yield a desired Ca/P ratio close to natural bone. It may be desirable to provide the second component in the amorphous or poorly crystalline state, as well.

In a preferred embodiment, DCPD is used as a participating promoter with a grain size less than 200 μm, in more preferred embodiments with an average grain size of <95 μm, and in most preferred embodiments with an average grain size of about 35–45 μm and a grain size maximum of less than about 110 μm.

In those cases where amorphous calcium phosphate is used as the sole precursor to produce the inventive PCA calcium phosphate it is important to control the natural tendency of the ACP to convert to highly crystalline hydroxyapatite. On the other hand, the rate of conversion and hardening should be fast enough to have surgical utility. One approach is to combine a precursor ACP containing an inhibitor of crystal formation (e.g. the ACP of Example 5) with an ACP that does not contain an inhibitor of crystal formation (e.g., a promoter). The reactants may be mixed in a dry state, with the appropriate particulate size and an excess of the inhibitor-containing ACP. The reactants can then be exposed to crystal-forming conditions such as the addition of water, followed by an elevation in temperature, such as that which occurs following introduction into the body, to convert the reactants to the PCA calcium phosphate of the invention. Unless steps are taken to further promote this reaction, the use of ACP as a promoter alone leads to a PCA calcium phosphate that does not tend to harden exceptionally well.

It is an interesting and unexpected feature of the inventive reaction that along with ACP, a participating promoter may likewise be converted to PCA calcium phosphate. This has been demonstrated experimentally for both DCPD and stoichiometric hydroxyapatite. Thus the conversion of a crystalline calcium phosphate to a less crystalline state in a substantially endothermic reaction has been shown for the first time.

While the conversion of ACP to PCA calcium phosphate has been demonstrated herein above, it is recognized that alternative materials may also be converted to a PCA calcium phosphate. Thus the production of a hydrated precursor paste from a crystalline calcium phosphate (including PCA calcium phosphate) in the presence of a limited amount of water in association with a net endothermic reaction at 37° C. and accompanied by paste hardening is considered within the scope of the invention. A preferred embodiment of this approach features a PCA calcium phosphate and a DCPD as reactants to produce a PCA calcium phosphate bioceramic Hydroxyapatite is a thermodynamically favored form of calcium phosphate. It is therefore also within the scope of the invention to promote the conversion of the reactive ACP into a PCA calcium phosphate in association with hardening of a hydrated precursor, through the use of promoters which themselves do not convert to PCA calcium phosphate (or hydroxyapatite). Suitable such promoters are termed "passive" and include, but are not limited to nucleation causing substances and catalysts. Particularly suitable in this regard are substances which provide reactive surfaces which weakly promote apatitic crystallization to produce a poorly crystalline apatitic calcium phosphate.

In one aspect, the invention features the use of passive promoters which are of limited solubility or insoluble in the aqueous liquid used to hydrate the ACP. Suitable promoters include, but are not limited to, metals, metal oxides, ceramics, silicates, sugars, salts, or polymeric particulate. For many applications preferred promoters will be themselves biodegradable. In general these substances are provided in granular form with a grain size in the range of 1 to 500 μm, preferably 1 to 300 μm, and most preferably 1 to 200 μm. The actual grain size used may be varied to improve the reaction promoting characteristics of the particular substance.

Table 2 of Example 3 reports the effect of a variety of passive promoters in the conversion of ACP to PCA calcium phosphate in the presence of a limited volume of water. Generally the promoter is present in an amount less than or equal to the ACP, and specifically in the range of about 1:1 to about 5:1 ACP:promoter. An amount of water (here, weight=volume, since density of water is one) approximately equal to the total weight of the two dry components is used to prepare a paste. Actual proportions of ACP, promoter and water can be conveniently determined by mixing the components in varying amounts and selecting the formulation which leads to a hardened PCA calcium phosphate at 37° C. in the desired amount of time. Preferred passive promoters include but are not limited to granular forms of $SiO_2$, mica, $Al_2O_3$, poly(L-lactide) (PLLA), polyglycolide (PGA), and poly(lactide-co-glycolide)(PLGA) copolymers.

Lastly, suitable enhancing promoters include, but are not limited to, water, heat, salts and additional calcium phosphate sources. In general these substances act to enhance the reactivity of ACP with a second calcium phosphate thereby promoting the conversion of ACP to PCA calcium phosphate. Conversion reactions may include acid/base, displacement, substitution, and hydrolysis reactions.

The inventive reaction permits one to design and modify the chemical composition of the resultant product, thereby providing a further mode of controlling bioactivity of the final product. Because the amorphous calcium phosphate tends to react completely with the other solids, the Ca/P of the resultant solid will be determined by the total calcium and phosphates present as starting materials. This permits reliable manufacture of PCA calcium phosphate products simply by selection of the relative proportions of the starting amorphous and secondary calcium phosphates. It is generally desirable to maintain a calcium to phosphate ratio of about 1.1–1.9, preferably less than 1.5, and most preferably about 1.4.

A particularly useful approach is to form the precursor paste into the approximate shape or size and then harden the material in vitro in a moist environment at 37° C. If desired, the hardened material may then be precisely milled or machined to the desired shape prior to use in the surgical setting. In those cases where storage of the hardened material is desired, it may be useful to enhance the stability of the inventive PCA calcium phosphate. In such cases, exposure of the pre-formed object to inhibitors of hydroxyapatite crystallization may be useful. Inhibitors may be added to the aqueous medium used to prepare the inventive PCA calcium phosphate calcium phosphate. Alternatively, the finished material or objects made from it may be exposed to an inhibitory substance. Suitable such inhibitors include but are not limited to magnesium, carbonate, pyrophosphate, poly L-glutamate, polyacrylate, phosvitin, casein, and protein-polysaccharides. Guidance for the use of such compounds can be found in Termine et al. *Arch. Biochem. Biophys.* 140:318–325 (1970) incorporated herein by reference. Storage at 4° C. or preferably colder temperatures such as −20° C., or −75° C. will also retard crystallization.

In the embodiments described above, the paste or putty is hardened at 37° C. Hardening at 37° C. is important for in vivo application of the hydrated precursor; however, the reaction proceeds at both higher and lower temperatures. This reactivity range may be taken advantage of when the paste or putty is to be hardened outside the body. In such cases, higher temperatures may be employed to further accelerate the hardening process. In this regard temperatures less than about 48° C. are preferred.

For in vitro hardening the use of a moist environment is useful (although not critical) because the reaction tends to consume water. In addition it is desirable to avoid evaporative water loss of the sample while it is hardening. Thus, use of a reaction chamber with a high ambient humidity is preferred (>80%, preferably 100% humidity). Alternatively the reaction and hardening process can often be performed under water.

The PCA calcium phosphate materials and composites of the invention are porous. Air dried samples can generally absorb water to an extent of 20% or more of their total volume. In many embodiments amounts of water greater than 30% of the total sample volume may be absorbed and in some preferred embodiments, water in amounts of greater than 40% preferably greater than 50% of the sample volume may be absorbed.

Any approach affecting the porosity of the hardened sample may be employed, although preferred approaches include the use of controlled compression molding for ex vivo fabrication and the use of specific promoter grain sizes for either ex vivo or in vivo hardening. The reaction may be performed in a chamber or mold to any pressure up to at least five tons.

In establishing new formulations of the inventive material it will be useful to know the nature and extent of the reaction. A number of tests for the identification of reaction products and reaction completeness may be used.

Hardness may be determined by simple inspection or manually probing the reaction product. The use of quantitative measures employing load cells and force transducers is however preferred. Hardness alone does not necessarily confirm conversion, although the inventive reactions have been designed so that hardening is accompanied by conversion.

Figure 18:
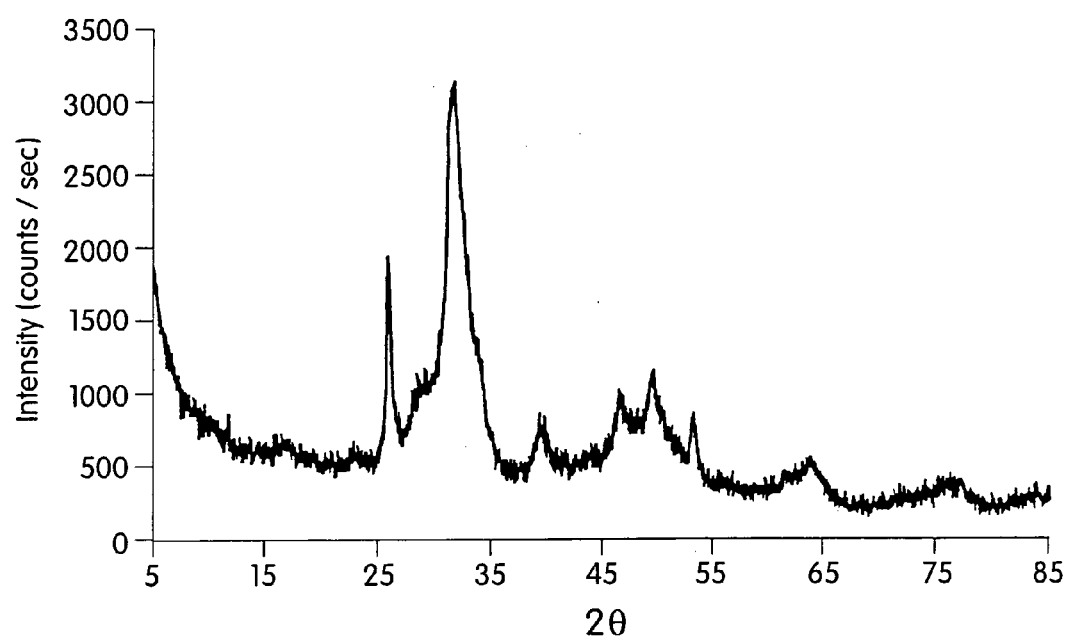
FIG. 18 is a full width XRD of the PCA calcium phosphate of the invention.

The X-ray spectra of the inventive PCA calcium phosphate is presented in FIG. 18. As can be seen from the figure the spectrum is characterized by broad peaks at approximately $2\theta=26$ and 32. An additional broad shoulder occurs at approximately $2\theta=29$ and another may be present at approximately $2\theta=33.6$. Absent from the spectra are any additional sharp peaks or sharp shoulders characteristic of crystalline hydroxyapatite occurring in the range of $2\theta=27–34$. In particular there are no sharp peaks or shoulders corresponding to Miller's Indices of 210, 112, or 300 for hydroxyapatite.

FTIR spectrum is characterized by peaks at 563 cm$^{-1}$, 1034 cm$^{-1}$, 1638 cm$^{-1}$ and 3432 cm$^{-1}$ (±2 cm$^{-1}$). Sharp shoulders are observed at 603 cm$^{-1}$ and 875 cm$^{-1}$, with a doublet having maxima at 1422 cm$^{-1}$ and 1457 cm$^{-1}$ (see, FIG. 6*c*).

For some embodiments it may be desirable to actually to have the presence of some unreacted crystalline calcium phosphate present following conversion (e.g. DCPD or hydroxyapatite). In such circumstances, the quantities of second calcium phosphate may be adjusted relative to the quantity of ACP present. Alternatively, reactions using a weaker promoter or less reactive ACP may also result in some unreacted starting materials. Mixtures of PCA calcium phosphate and DCPD, or PCA calcium phosphate and hydroxyapatite or PCA calcium phosphate and other reactants are within the scope of the invention. In some limited cases, the use of PCA calcium phosphate itself (provided it has a significant amorphous character) in place of ACP is possible.

An implantable bioceramic material may be prepared in precursor form as a paste or putty by addition of a fluid to the precursor materials and mixing, The precursor materials may include an ACP, a promoter and additional supplementary materials if required (in some cases some or all of these constituents may be partially pre-hydrated). The mixing of the components may occur in any convenient order. The components may be mixed and/or physically ground prior to the addition of fluid. Alternatively fluid may be added to a single dry component, and then additional dry components added to complete the paste.

A wide variety of proportions of reactants may be used, in most cases the absolute ratio of constituents will depend on the circumstances of the intended use. For systems employing only an ACP and a participating promoter the reactants will generally be used in equal amounts by weight. Water will also be added in a weight approximately equal to the combined weight of the other dry reactants.

In a preferred embodiment, a DCPD with grain size distribution similar to distribution B3 from Example 10 and a highly reactive carbonated ACP from Example 5 with an ACP:DCPD ratio of 0.5 g:0.5 g may be combined with water in amounts ranging from 0.7 to 1.3 mL.

In the case of reactions involving passive promoters and ACP alone, it has been found that ACP:promoter proportions in the range of about 5:1 to 1:1 work well. For a total weight of reactants of 1 gram, 0.5 to 1.5 mL water may be used.

Empirical determination of appropriate amounts of reactants and water may be made by (a) establishing ratios of dry components and water that lead to the formation of a workable paste or putty; (b) selecting those formulations which lead to hardening in a suitable amount of time (most often 20 to 60 minutes) at 37° C.; and/or (c) testing the performance of the selected formulations in a suitable model system (e.g. in vivo subcutaneous resorption or in vitro tissue culture resorption models).

In some preferred embodiments (e.g., Examples 8–10), the reaction occurs slowly at room temperature and is almost undetectable below 18 or 19° C. (see DSC example). The reaction is accelerated at higher temperatures, and particularly at body temperature. This property is particularly useful in a surgical situation, since the hydrated precursor paste formed by mixing reactants with a limited volume of water remains injectable and/or formable for a considerable period of time (up to several hours) while held at room temperature, provided care is taken to prevent evaporative moisture loss. Thus, at room temperature in air (ca. 22° C.) the paste hardens after a time greater than one hour and remains formable and/or injectable for longer than 10 minutes, and preferably longer than one hour and most preferably longer than three hours. Following injection at the implant site (ca. 37° C.), the paste hardens in less than about an hour, preferably in about 10–30 minutes. When held at 4° C. the paste is not hard even after several days, provided care has been taken to prevent evaporative moisture loss. Alternatively, once the material has been implanted, hardening can be accelerated by application of heat to the implant. Heat may be applied through the use of lasers, ultrasound, and the like, or by other means including the use of pharmaceuticals to locally raise or lower the body temperature.

Depending upon the amount of fluid added, the mixture of an ACP and a promoter results in a hydrated precursor mixture with varying consistency. By selecting the appropriate amount of liquid to be added to the reactants, the viscosity of the precursor paste may be adjusted according to need. The paste may be prepared either with an injectable or a formable consistency or it may be prepared with just enough liquid to be both injectable and formable.

Injectable paste is generally prepared by mixture of the reactants in an amount of water or buffer sufficient to produce the desired consistency for injection. Most often this will be as thick as possible while still being able to be passed through a 16–18 gauge syringe. For some formulations requiring injection directly into solid tissue (e.g. into cortical bone of an osteoporosis patient) thinner consistencies (e.g., 1.5 mL $H_2O$/g dry precursors) may be desired. Because of the low crystallinity of the component solids in the paste, the material has markedly improved flow characteristics over prior art compositions. Flow characteristics of the resultant paste are toothpaste-like while prior art materials inherit a granular or oat meal-like consistency. The paste may be prepared before use, up to a period of several hours if held at room temperature and evaporative water loss is minimized. Even when steps are taken to minimize evaporation, holding at room temperature is sometimes accompanied by drying out of the hydrated materials. In such instances, a small amount of water may be added and mixed to restore the desired consistency. The storage time may be extended by maintaining the paste at reduced temperatures in the range of 1–10° C. in the refrigerator provided steps are taken to minimize evaporative water loss.

In another preferred embodiment, a formable paste or putty may be prepared, which can be introduced into the implant site. The formable precursor is generally prepared by mixture of the dry reactants in an amount of water or buffer sufficient to produce the desired consistency for forming. Most often this will be as thick as possible while still being formable by hand, although thinner more flowable consistencies may be desirable for many applications. In many embodiments the preferred consistency will be similar to that of clay or glazing compound. The hydrated material may be prepared before use, up to a period of several hours if held at room temperature or below and evaporative water loss is minimized. The storage time may be extended by maintaining the hydrated material at reduced temperatures in the range of 1–10° C. in the refrigerator provided steps are taken to minimize evaporative water loss.

Application to the implant site will be performed according to the nature of the specific indication and the preferences of the surgeon. Similar considerations apply for cartilaginous implants as for bone. Injection techniques will be employed to deliver the inventive PCA calcium phosphate precursors directly into hard tissue (e.g. for osteoporosis patients) or into small fractures. For larger fractures putty-like consistencies will be preferred and will be implanted by hand or with a spatula or the like. Reconstruction will often use putty-like forms but in some instances it will be more advantageous to pre-form, harden, and shape the material ex-vivo and implant a hardened form. Exposure or mixing of the material with blood or body fluids is acceptable and in many cases will be preferred as a method to promote osteo- or chondrogenesis. Implantation into soft tissues may employ any of the above approaches.

Formation of the reactive amorphous calcium phosphate. In preferred embodiments an ACP is converted in the presence of a promoter and water to PCA calcium phosphate. The use of an amorphous calcium phosphate, which can react quickly and completely to a product PCA calcium phosphate without significant further crystallization, provides a novel route to a highly resorbable calcium phosphate, with a variety of medical uses. The promoters of the instant invention promote conversion and hardening either by direct participation as a reactant along with ACP, or passively by serving as catalysts, nucleators or reaction enhancing agents, or in a combination of modes.

Not all ACPs have the same reactivity with a given promoter, and their reactivity is generally compared relative to their reactivity with a DCPD of grain distribution similar to B1 in Table 3. Examples 10 and 11 describe a variety of ACPs which have been tested for reactivity with such a DCPD. Use of a stronger DCPD promoter with a smaller grain size facilitates the reaction with weakly-reactive or otherwise un reactive ACPs. Generally less reactive ACPs will require the use of stronger promoters and in some cases combinations of promoters.

In a preferred embodiment, a highly reactive ACP is employed. Hydrated precursors comprising this ACP are capable of undergoing hardening and conversion either in the presence of a strong promoter such as a DCPD with small grain size (e.g. <63 μm) or in the presence of a relatively weak promoter such as a DCPD sample comprising a substantial amount of grains greater than 100 μm (e.g. distribution B1). One highly reactive ACP is a carbonated ACP which has been activated by heat treatment for approximately one hour at 460° C.

The invention also provides a test for identifying suitable reactive precursors for the inventive PCA calcium phosphate. The test comprises combining an amorphous calcium phosphate, DCPD, and water, producing a hydrated PCA calcium phosphate precursor substance and demonstrating its ability to harden in about 10 to 60 minutes at or around body temperature. Reactants found to produce hardened PCA calcium phosphate in this test may then be placed intramuscularly in a test animal and checked for biological resorbability. One hundred milligrams (100 mg), and preferably three hundred milligrams (300 mg), of PCA calcium phosphate thus prepared will resorb in less than 12 months, preferably less than 6 months and most preferably in less than 2 months in a rat muscle. Further 80% of one gram/ laced intramuscularly will be resorbed in the same time frame. Alternatively, at least 2 g placed subcutaneously will be fully resorbed in rat in less than 12 months, preferably less than 6 months and most preferably in less than 2 months. For the identification of less reactive forms of ACP it is preferred to use a weak DCPD promoter. Similar tests may also be established using other participant or passive promoters.

The method of the present invention permits initial formation of amorphous calcium phosphate particles of less than 1000 Å, preferably 200–500 Å, and most preferably 300 Å, the further growth of which are curtailed by rapid precipitation of the product from solution. In FIG. 1, a high-resolution transmission electron micrograph is shown to illustrate the morphological characteristics and the angstrom-scale nature of the preferred reactive amorphous calcium phosphate of the invention. Note the unclear boundaries separating the globule-like clusters, lacking clear edges and surfaces, in contrast to crystalline material.

During reaction of calcium and phosphate ion sources to form an amorphous calcium phosphate, a third ion may be introduced in the solution so that these ions are incorporated in the amorphous precipitate structure instead of trivalent $PO_4^{3-}$ group(s). Because some $PO_4^{3-}$ is replaced by the third ion, the overall $PO_4^{3-}$-decreases, thus increasing the Ca/P ratio of the amorphous precipitate (as compared to standard amorphous calcium phosphate) and modifying the valence or charge state of the calcium phosphate. The amorphous solids then may be rapidly freeze-dried to preserve the chemical and physical properties of the material. The amorphous solids then may be treated under specific conditions selected to promote removal of at least some of the third ion. In the case of carbonate, specific temperature and pressure conditions lead to the reduction of total carbon, presumably as gaseous carbon dioxide from the amorphous solid, while maintaining the amorphicity.

The source of the enhanced reactivity is not completely understood; however, it is believed to be associated with the degree of amorphicity (lack of crystallinity) and, in some embodiments, site vacancies in the material, as created by the process of the present invention. Site vacancies as envisioned herein refer to the lack of one pair of an ion pair (e.g. $CO_3^{2-}$) missing from $CaCO_3$ in a material containing many ion pairs. The presence of site vacancies may provide reactive sites for subsequent reaction. This stoichiometric imbalance may be responsible for the increased reactivity of the amorphous calcium phosphate The reactive ACP is a substantially amorphous solid with a higher Ca/P ratio than is typically found in amorphous calcium phosphates, which has generally been reported in the past to be about 1.50.

The amorphous state is induced by controlling the rate and duration of the precipitation process. The amorphous hydroxyapatite of the present invention is precipitated from solution under conditions where initial precipitation is rapid. Rapid crystal or grain growth enhances the number of defects within each grain, thereby increasing solubility. At the extreme end of the spectrum, crystal or grain growth is so rapid and defect density is so significant that an amorphous calcium phosphate results. Amorphous calcium phosphate is gel-like and includes solid solutions with variable compositions. These gels have no long range structure, but are homogeneous when measured on an Angstrom scale. Under physiological conditions, these amorphous compounds have high solubilities, high formation rates and high rates of conversion to PCA calcium phosphate.

The amorphous calcium phosphate solids produced by this method retain their amorphous nature sufficiently long enough to be introduced into the final reaction as substantially amorphous solids.

In one embodiment of the present invention, a solution is prepared which contains calcium and phosphate ions and a third ion in a concentration, at a pH and at a temperature which will promote the rapid nucleation and precipitation of calcium phosphate. When precipitation is sufficiently rapid, an amorphous gel-like calcium phosphate is formed. Because the thermodynamically favored crystalline form of hydroxyapatite is enhanced by reducing the rate of reaction, certain processing steps of increasing the rate of reaction may be taken to ensure that an amorphous compound is obtained. The following factors, among others, are to be considered when designing a solution for the rapid precipitation of the amorphous calcium phosphate of the present invention.

Preferred conditions: Rapid mixture of calcium and phosphate sources to increase the rate of reaction. The rate of reaction is increased to favor non-stable phases as a product. Allowing more reaction time for each of the ions to juxtapose correctly to form a solid will result in a more thermodynamically favorable crystalline and stable structure.

Preferred calcium and phosphate sources: The use of highly concentrated or near supersaturation solutions ensures that a more rapid reaction will occur.

Preferred temperature: Although the reaction can be carried out at room temperature, temperatures of near boiling point to increase the concentration of one reactant is a possible means of increasing the rate of reaction.

In one embodiment, an aqueous solution of calcium ions, phosphate ions and carbonate ions are mixed together rapidly to obtain a carbonate containing amorphous calcium phosphate solid. The relative concentrations of the ions are selected to give a precipitate having the desired Ca/P ratio. The carbonate ion substitutes for a phosphate ion in the amorphous calcium phosphate. The carbonated amorphous calcium phosphate may be obtained by precipitation from an aqueous carbonate solution. Suitable aqueous carbonate solutions include, by way of example only, bicarbonate solution, sodium carbonate solution, potassium carbonate solution. It is further contemplated as within the scope of the invention to use non-aqueous solutions.

Use of a carbonated material is desirable because it permits manipulation of the Ca/P ratio by substitution of $PO_4^{3-}$ by $CO_3^{2-}$. Additionally, the presence of $CO_3^{2-}$ is known to retard the development of crystallinity in amorphous calcium phosphate. It is recognized, however, that other ions or a mixture of ions may be suitable in place of or in addition to carbonate ion in modifying the Ca/P ratio and in introduction of reactive site vacancies into the amorphous calcium phosphate, such as by way of example only, nitrate, nitrite, acetate, $Mg^{+2}$ and $P_2O_7^{4-}$ ions.

The amorphous calcium phosphate precipitate may be collected and filtered prior to activation. It is preferred to perform this step in a cold room or at sub-ambient temperatures so as to preserve the amorphous state of the precipitate collected. Collection may typically may be carried out by any conventional means, including, but in no way limited to gravity filtration, vacuum filtration or centrifugation. The collected precipitate is gelatinous and is washed more than once with distilled water.

The washed precipitate is then dried under any conditions which maintain the amorphous character of the material. Lyophilization is a suitable, but not exclusive, technique.

Upon freezing, the precipitate while kept frozen, is dried to remove the bulk of the entrained liquid. This procedure may be accomplished by placing the frozen precipitate into a vacuum chamber for a given period of time. Freeze-drying typically occurs at liquid nitrogen temperatures for a time in the range of 12–78 hrs, preferably about 24 hours, and under a vacuum in the range of $10^{-1}$–$10^{-4}$, preferably $10^{-2}$, torr. A preferred method includes lyophilization because the cryogenic temperatures typically used in lyophilization inhibit further crystallization of the material. As a result, the amorphous calcium phosphate obtained thereby is an extremely fine free flowing powder.

The dried ACP may then be activated to a highly reactive ACP. In a preferred embodiment, where carbonate is present in the ACP, the ACP powder is heated to drive off remaining free water, water of hydration, and to remove carbon, presumably through the decomposition of $CO_3^{2-}$ into $CO_2$ and oxygen. The heating step is carried out at a temperature of less than 500° C. but more than 425° C., so as to prevent conversion of the amorphous calcium phosphate into crystalline hydroxyapatite. Heating is preferably carried out at a temperature in the range of 450–460° C. for 1 to 6 hours preferably for 50 to 90 minutes.

Atmospheric pressure is used for convenience in most of the embodiments for production of ACP described herein. However, the use of vacuum with appropriate temperatures is considered to be within the scope of the invention.

To produce a highly reactive ACP it is desirable to maintain the amorphous property of the material throughout the entire ACP synthesis. If significant crystallinity in its entirety (single crystalline regions) or even in local domains (microcrystalline regions) is introduced during the process or in the final product, the solid has been found to become less reactive. The resultant highly reactive calcium phosphate is amorphous in nature and has a calcium to phosphorous ratio in the range of 1.55 to 1.65. In a preferred embodiment, the amorphous calcium phosphate has a Ca/P ratio of about 1.58.

Low crystallinity and site vacancies (porosity and/or stoichiometric changes) may account for the observed higher reactivity of the amorphous calcium phosphate of the present invention. This is supported by the following observations: a.) A carbonate-containing amorphous calcium phosphate which has been heated to 525° C. is observed to have an increased crystalline content and to have a corresponding decrease in reactivity. b.) Amorphous calcium phosphate that is heated to only 400° C. retains its amorphous characteristic, but exhibits a decreased reactivity. c.) Non-carbonated ACPs heated to 460° C. have been studied using the DCPD reaction (as described in example 8) and while reactive with a strong DCPD promoter were not reactive with a weak DCPD promoter.

These observations suggest that both amorphicity and decreased carbon content (vacant reactive sites) are a factor in reactivity. This is not intended to be in any way an exclusive explanation for the basis of reactivity. Other basis for the observed reactivity are considered to be within the scope of the invention.

Figure 4A:
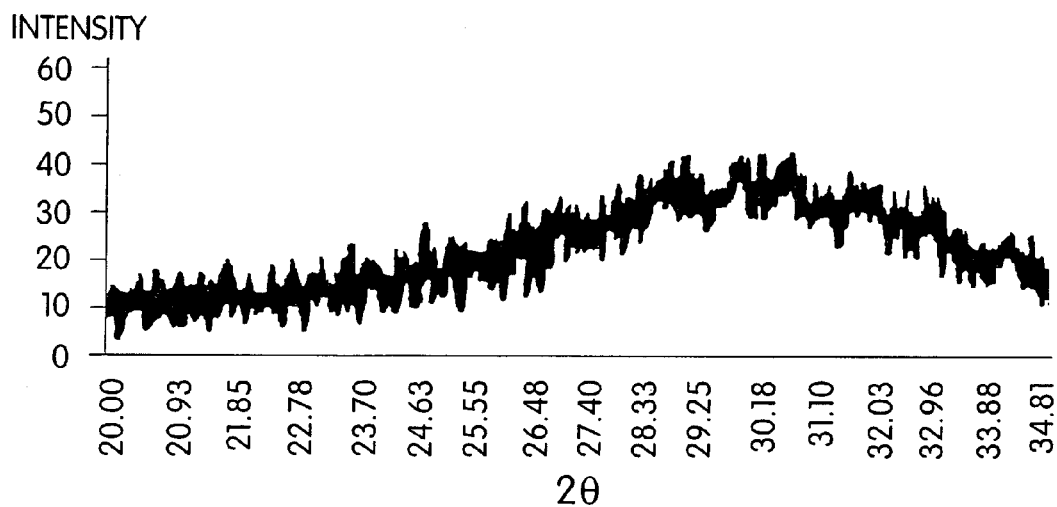
FIG. 4 are X-ray diffraction patterns of (a) reactive amorphous calcium phosphate; and (b) dicalcium diphosphate used in a reaction to form a bone substitute material of the invention.
Figure 17A:
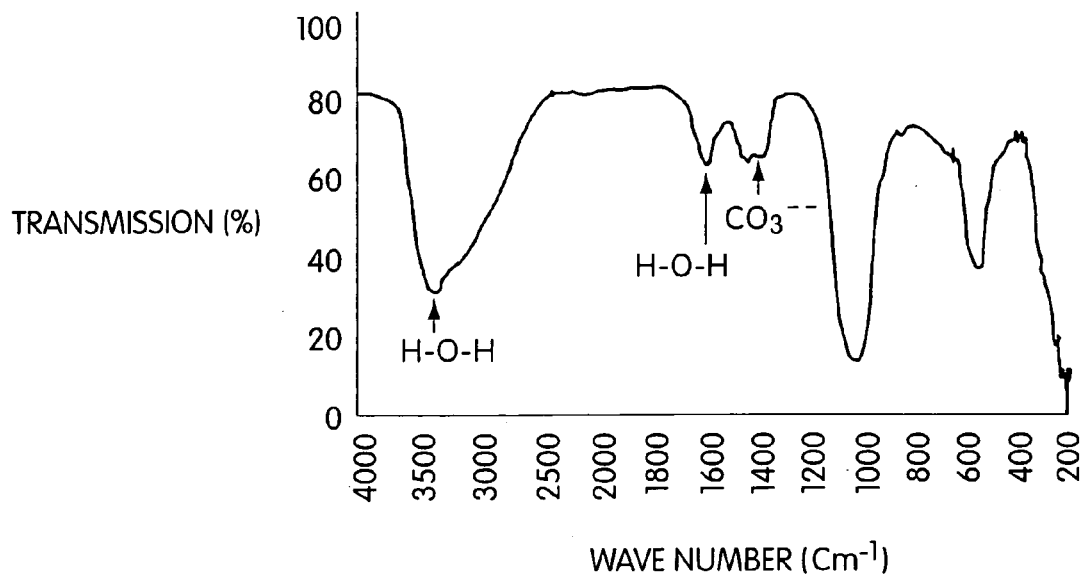
FIG. 17 is infrared spectra of the amorphous calcium phosphate material before heat treatment (FIG. 17a) and after heat treatment (FIG. 17b)
Figure 17B:
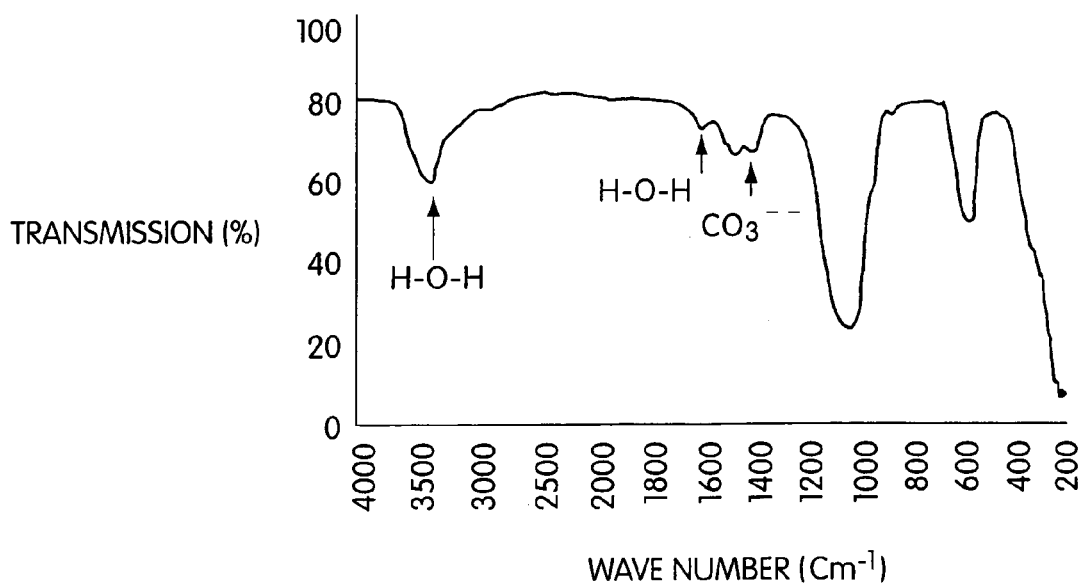

The resulting amorphous calcium phosphate powder is a highly reactive amorphous calcium phosphate material with a Ca/P ratio of between 1.1–1.9, preferably about 1.55 to 1.65, and most preferably about 1.58. FIG. 17a and 17b illustrate the infrared spectra of the amorphous calcium phosphate after lyophilization process (FIG. 17a) and after the subsequent heat treatment at 450° C. for 1 hr (FIG. 17b). Infrared peaks illustrating presence of local chemical groups in the material show that the presence of H—O—H (at approximately 3,400 $cm^{-1}$ and 1640 $cm^{-1}$) and $CO_3^2$ group (at 1420–1450 cm-1) are significantly reduced after heat treatment. However, the x-ray diffraction patterns in FIG. 4a of heat activated ACP demonstrate that the amorphous state is retained after heating and lyophilization. The XRD pattern is characterized by broad peaks and undefined background with absence of sharp peaks between 2θ20 to 35 or at any diffraction angles that correspond to known crystalline calcium phosphates.

Figure 2:
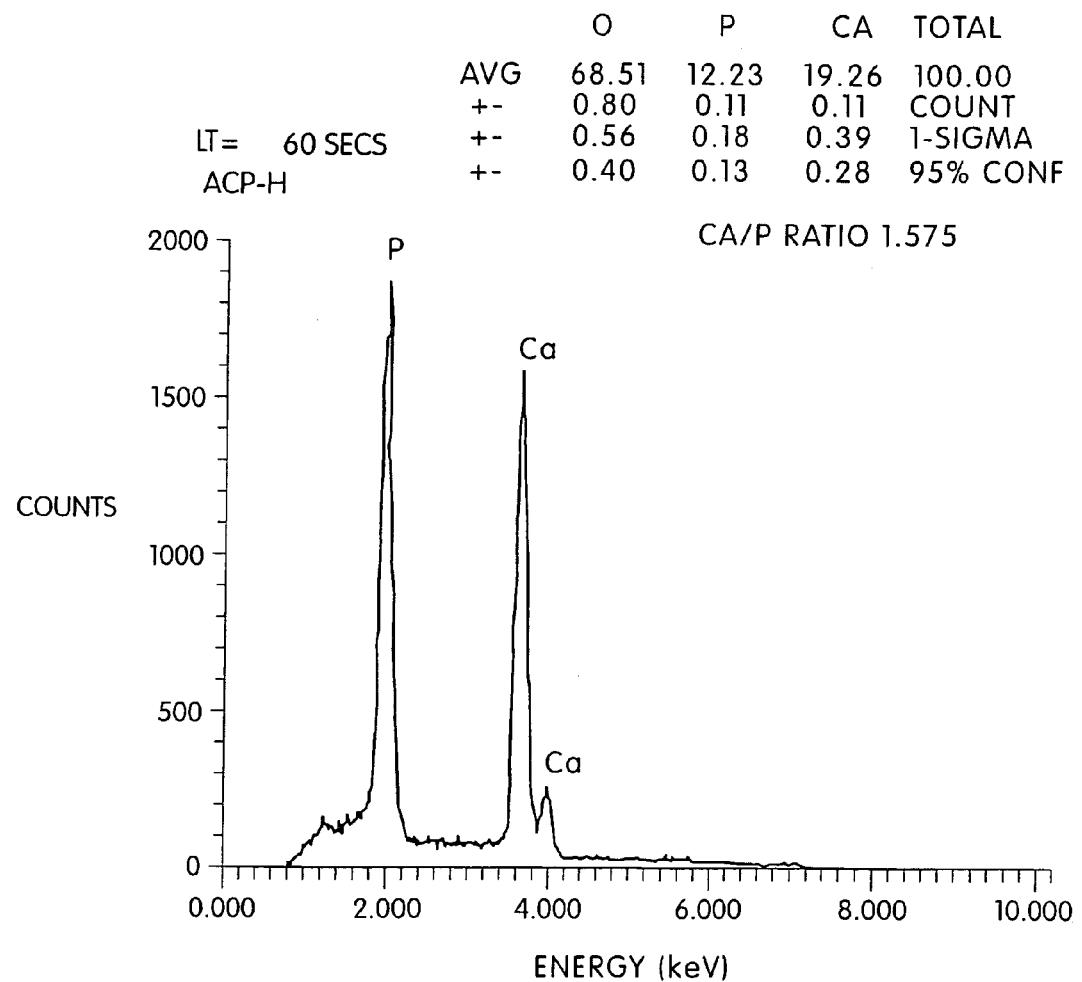
FIG. 2 is an energy-dispersive electron microprobe spectrum of the reactive amorphous calcium phosphate of the present invention after the vacuum heating procedure which yielded Ca/P to be 1.58.

The Ca/P measurement performed using wave length-dispersive X-ray analysis on an electron micro-probe of the same material after heat treatment yields Ca/P to be 1.58 (FIG. 2).

These characterizations demonstrate that although there is a change in the local moiety of certain groups in the amorphous calcium phosphate solids, the overall amorphicity is maintained throughout the process.

The preparation of the PCA calcium phosphate calcium phosphate as a composite material may sometimes be desirable in order to provide an implant with different properties than the inventive PCA calcium phosphates. Furthermore, the consistency, formability and hardness of the PCA calcium phosphate calcium phosphate, as well as the reaction speed, may be varied according to the therapeutic need by selection of the appropriate supplementary materials from which to prepare the implantable bioceramic composite material of the invention.

Composites may be prepared by combining the PCA calcium phosphate calcium phosphate of the invention with a selected supplementary material. The PCA calcium phosphate calcium phosphate phase may serve as a reinforcing material, a matrix or both. The PCA calcium phosphate calcium phosphate of the invention in it's initial paste form in preferred embodiments typically maintains a pH of about 6–7 and is therefore compatible with a wide range of additives without deleterious effect. The supplementary material is selected based upon its compatibility with calcium phosphate and its ability to impart properties (biological, chemical or mechanical) to the composite, which are desirable for a particular therapeutic purpose. For example, the supplementary material may be selected to improve tensile strength and hardness, increase fracture toughness, alter elasticity, provide imaging capability, and/or alter flow properties and setting times of the bone substitute material. The supplementary materials are desirably biocompatible, that is, there is no detrimental reaction induced by the material when introduced into the host.

The supplementary material may be added to the PCA calcium phosphate calcium phosphate in varying amounts and in a variety of physical forms, dependent upon the anticipated therapeutic use. The supplementary material may be in the form of sponges (porous structure), meshes, films, fibers, gels, filaments or particles, including micro- and nanoparticles. The supplementary material itself may be a composite. The supplementary material may be used as a particulate or liquid additive or doping agent which is mixed intimately with the resorbable PCA calcium phosphate calcium phosphate. The supplementary material may serve as a matrix for the PCA calcium phosphate which is embedded or dispersed within the matrix. Alternatively, the PCA calcium phosphate may serve as a matrix for the supplementary material, which is dispersed therein. The supplementary material may be applied as a coating onto a PCA calcium phosphate body, for example, as a post-fabrication coating to retard resorption time or otherwise affect the bioceramic material properties. Due to the high porosity and water absorption characteristics of the inventive PCA calcium phosphates, solid PCA calcium phosphate may be impregnated with water soluble polymers by simple immersion in the aqueous polymer solution. Lastly, the supplementary material may be coated with PCA calcium phosphate.

In most instances, the supplementary material will be biocompatible and in many instances, it is desirable that the supplementary material also be bioresorbable. In many preferred embodiments, the supplementary material will have an affinity for calcium, phosphate or calcium phosphates which will enhance the strength of the hydroxyapatite/supplementary material interface. The affinity may be specific or mediated through non-specific ionic interactions. Suitable bioerodible polymers for use as a matrix in the composite include, but are not limited to, collagen, glycogen, chitin, celluloses, starch, keratins, silk, nucleic acids, demineralized bone matrix, derivatized hyaluronic acid, polyanhydrides, polyorthoesters, polyglycolic acid, polylactic acid, and copolymers thereof. In particular, polyesters of a hydroxycarboxylic acids, such as poly(L-lactide) (PLLA), poly(D,L-lactide) (PDLLA), polyglycolide (PGA), poly(lactide-co-glycolide)(PLGA), poly(D,L-lactide-co-trimethylene carbonate), and polyhydroxybutyrate (PHB), and polyanhydrides, such as poly(anhydride-co-imide) and co-polymers thereof are known to bioerode and are suitable for use in the present invention. In addition, bioactive glass compositions, such as compositions including $SiO_2$, $Na_2O$, $CaO$, $P_2O_5$, $Al_2O_3$ and/or $CaF_2$, may be used in combination with the poorly crystalline hydroxyapatite of the invention. Other useful bioerodible polymers may include polysaccharides, peptides and fatty acids.

Bioerodible polymers are advantageously used in the preparation of resorbable hardware, such as pins, screws, plates and anchors for implantation at a bone site. In preferred resorbable hardware embodiments, the supplementary material itself is resorbable and is added to the PCA calcium phosphate in particulate or fiber form at volume fractions of 1–50% and preferably, 1–20 wt %. In some preferred embodiments, the resorbable fiber is in the form of whiskers which interact with calcium phosphates according to the principles of composite design and fabrication known in the art. Such hardware may be formed by pressing a powder particulate mixture of the poorly crystalline apatitic calcium phosphate and polymer. In one embodiment, a PCA calcium phosphate matrix is reinforced with PLLA fibers, using PLLA fibers similar to those described by Tormala et al., Clin. Mater. 10:29–34 (1992) for the fabrication of biodegradable self-reinforcing composites.

The resorbable nature of the inventive PCA calcium phosphate as well as its ability to benignly interact with and adsorb proteins, nucleic acids, and other substances make it an ideal substance for use as an implantable depot for use in the delivery of therapeutic substances to the body. In general, the main requirement is that the agent to be delivered remains active in the presence of the vehicle during fabrication and/or loading, or be capable of subsequently being activated or reactivated. The stability and/or compatibility of a particular agent with the inventive material, as well as fabrication strategies, may be tested empirically in vitro. Some representative classes of useful biological agents include organic molecules, proteins, peptides, nucleic acids, nucleoproteins polysaccharides, glycoproteins, lipoproteins, and synthetic and biologically engineered analogs thereof.

In one aspect of the invention, bone regenerative proteins (BRP) are incorporated into the inventive PCA calcium phosphate. BRPs have been demonstrated to increase the rate of bone growth and accelerate bone healing. A bone graft including the inventive PCA calcium phosphate and BRP is expected to promote bone healing even more rapidly than a bone graft using the calcium phosphate of the present invention alone. The efficacy of BRP is further enhanced by controlling PCA calcium phosphate resorption such that it dissolves at a rate that delivers BRP, calcium, and phosphorus at the optimum dosage for bone growth. Such a method of incorporating BRP would include, but is limited to, mixing a buffer solution containing BRP with its optimum pH that would maintain protein activity, instead of distilled water. Exemplary BRPs include, but are in no way limited to, Transforming Growth Factor-Beta, Cell-Attachment Factors, Endothelial Growth Factors, and Bone Morphogenetic Proteins. Such BRPs are currently being developed by Genetics Institute, Cambridge, Mass.; Genentech, Palo Alto, Calif.; and Creative Biomolecules, Hopkinton, Mass.

In another embodiment of the invention, it is contemplated to incorporate antibiotics or agents into the amorphous calcium phosphate and its mixture. From a clinical sense, one of the major implication arising from a bone-graft surgery is a need to control the post-operative inflammation or infection. A bone graft including the inventive PCA calcium phosphate and antibiotic(s) is expected to reduce the chances of local infection at the surgery site, contributing to infection-free, thus faster bone healing process. The efficacy of antibiotics is further enhanced by controlling their release from the PCA calcium phosphate delivery vehicle by regulating the resorption rate such that it dissolves at a rate that delivers antibiotic peptides or its active component at the most effective dosage to the tissue repair site. Exemplary antibiotics include, but are in no way limited to, Penicillin, Chlortetracycline hydrochloride (Aureomycine), Chloramphenicol and Oxytetracycline (Terramycine). Both antibiotics, mostly polypeptides, and bone regenerating proteins may be intermixed with the PCA calcium phosphate material of the present invention, to locally deliver all or most of the necessary components in facilitating optimum condition for bone tissue repair.

Non resorbable apatitic bone fillers and cements may also be prepared by the methods of the current invention by promoting the conversion of ACP to a more crystalline state than PCA calcium phosphate. In general use of more hydroxyapatite stoichiometric Ca/P ratios decrease use of crystallization inhibitors, and crystallization promoting conditions such as elevated temperatures will tend to drive the conversion to a more crystalline product.

The invention is further exemplified with reference to the following examples, which are presented for the purpose of illustration only and are not to be considered as limiting of the invention.

EXAMPLE 1

Production of PCA calcium phosphate using an ACP and participating promoters. This example demonstrates the hardening properties and PCA calcium phosphate formation from ACP using a number of different participating promoters. Highly reactive ACP was prepared according to Example 5.

The nanocrystalline hydroxyapatite of samples 1—1,1-2 and 1-3 were prepared without inhibitors of crystallization as follows: 218 g of disodium hydrogen orthophosphate ($Na_2HPO_4 \cdot 12H_2O$) were dissolved in 1200 mL of solution of distilled water. For carbonated PCA calcium phosphate of samples 1—1 and 1-2, 80 g of $NaHCO_3$ were also added to this solution. 70 g of calcium nitrate [$Ca(NO_3)_2 \cdot 4H_2O$] were dissolved in 500 mL of distilled water. The calcium solution was quickly poured into the phosphate solution at room temperature with constant stirring. Precipitation was immediate and substantially complete. The pH of the precipitate was adjusted to 7.4 by the addition of sodium hydroxide solution in order to avoid the formation of acidic calcium phosphates. The precipitate was immediately separated from the solution by filtration through a Buchner filter (with a total surface about 0.1 sq.m), and was washed by about 3 liters of distilled water. A gel cake of low crystallinity calcium phosphate was obtained on the filter paper. A portion of the gel cake was immediately lyophilized for samples 1-2 and 1-3.

For sample 1—1 the gel cake was treated as follows: After filtration and washing, an appropriate amount of distilled water (5 to 80 weight %) was added to the gel precipitate. The gel was homogenized by whipping energetically for a few minutes. It was then cast into polytetrafluoroethylene (PTFE) molds (diameter 60 mm; height 2 mm), and sonicated for a few minutes in order to release the air bubbles trapped in the gel.

The molds were dried in a chamber at controlled temperature (5 to 37° C.) and humidity (10 to 95% RH). The samples shrank slowly on drying and released most of their water. The rate of drying and the shrinkage of the samples depended on the initial water content. The material hardened on drying and became glassy. It contained about 10% of residual water.

The remaining hydroxyapatites and calcium sources were used as is from commercial sources.

hydroxyapatite hardened more slowly and less completely than the smaller grain size hydroxyapatite.

EXAMPLE 2

This example demonstrates the use of a neutral apatitic calcium phosphate as a promoter for the conversion of ACP to the inventive PCA calcium phosphate to promote bone growth in vivo. Stoichiometric hydroxyapatite is mixed with reactive ACP as described in Example 1-4. Hydrated precursor paste is applied to animal subjects as described in Examples 15, 16 or 19. Bone healing and biocompatibility is monitored as described at the time points indicated.

EXAMPLE 3

This example demonstrates the production of PCA calcium phosphate from ACP using a number of different passive promoters.

Figure 13:
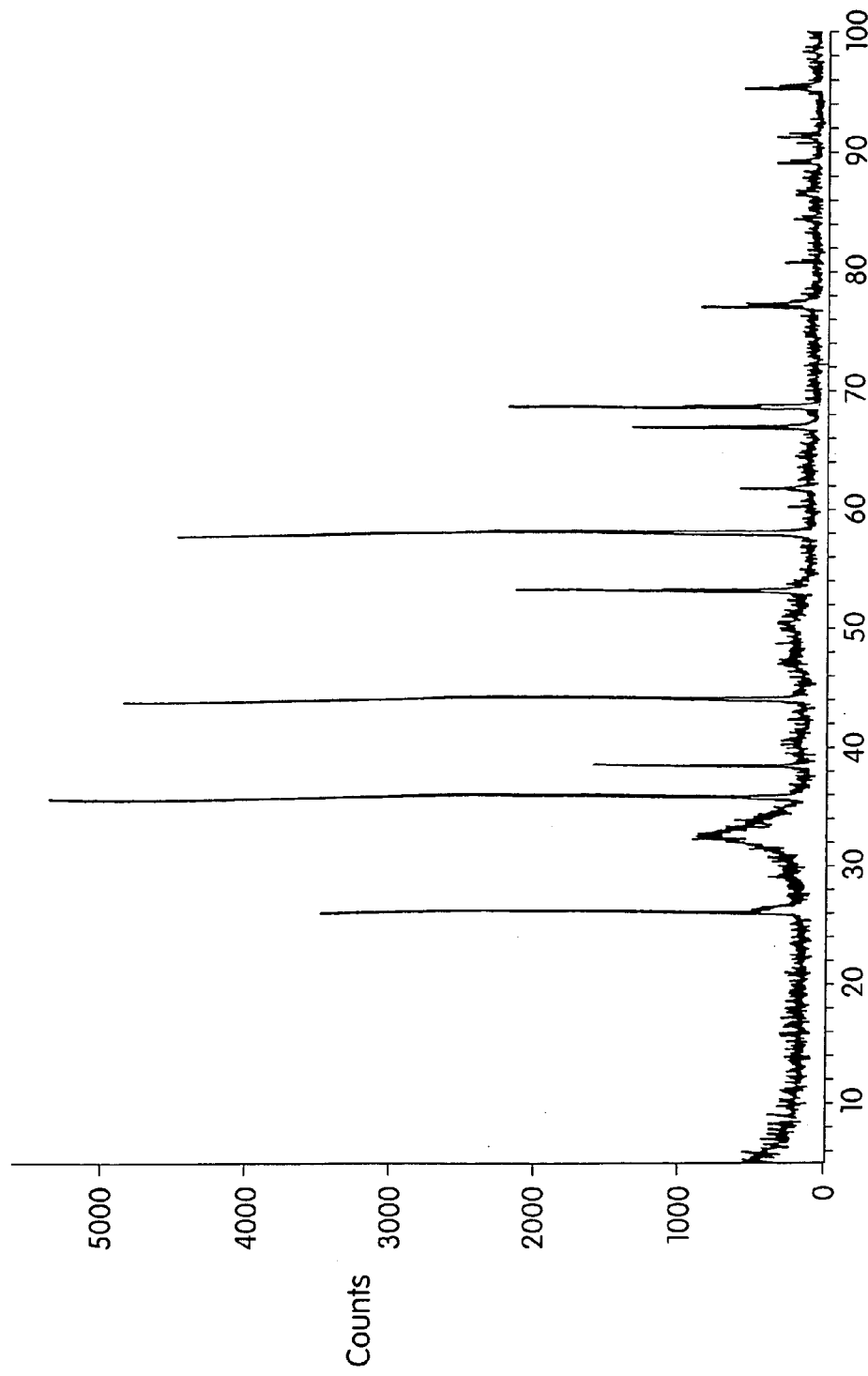
FIG. 13 is an X-ray diffraction patterns of PCA calcium phosphate prepared from $Al_2O_3$ passive promoter, in which $Al_2O_3$ peaks are indicated by lines and the characteristic PCA material pattern clearly visible in the range of $2\theta = 24°-34°$.

Highly reactive ACP was prepared according to Example 5. ACP was mixed with the specific promoter at a ratio (wt/wt) of about 5:1 or 1:1 (see Table 2) for 5 minutes in a SPEX laboratory mill. Water (0.75–0.85 mL) was added and mixed to form a putty. The mixture was then formed into a ball, wrapped in moist tissue paper and heated to 37° C. for at least 30 minutes. After 30 minutes and at various time points thereafter the paste was monitored for hardness. FIG. 13 is a representative XRD from sample 2-4 employing an alumina promoter. In this figure the alumina peaks can be seen superimposed over the standard PCA calcium phosphate profile.

TABLE 1

ACP Conversion Using Participating Promoters

| sample | participating promoter | incubation at 37° C. | extent of hardening | PCA* by FTIR | PCA* by XRD |
|---|---|---|---|---|---|
| 1-1 | carbonated nanocrystalline hydroxyapatite, air dried | 30 min 2 hrs | starting to set hard | yes | ND |
| 1-2 | carbonated nanocrystalline hydroxyapatite, lyophilized | 30 min 2 hrs | hard hard | yes | yes |
| 1-3 | non-carbonated nanocrystalline hydroxyapatite, lyophilized | 30 min 2 hrs | starting to set hard | yes | ND |
| 1-4 | Aldrich hydroxyapatite grain size < 15–30 μm | 30 min | hard | yes | yes |
| 1-5 | Clarkson hydroxyapatite grain size > 250 μm | 30 min | starting to set | yes | ND |
| 1-6 | Monetite - non calcinated grain size | 30 min 15 hrs | soft starting to set | yes | ND |
| 1-7 | $CaCO_3$ | 30 min 15 hrs | starting to set | yes | ND |
| 1-8 | $Ca(OH)_2$ | 30 min 15 hrs | soft starting to set | yes and $Ca(OH)_2$ | ND |
| 1-9 | $Ca(CH_3COO)_2$ | 30 min 15 hrs | soft soft | yes | ND |

*PCA = poorly crystalline apatitic calcium phosphate
ND = analysis not done

Figure 14:
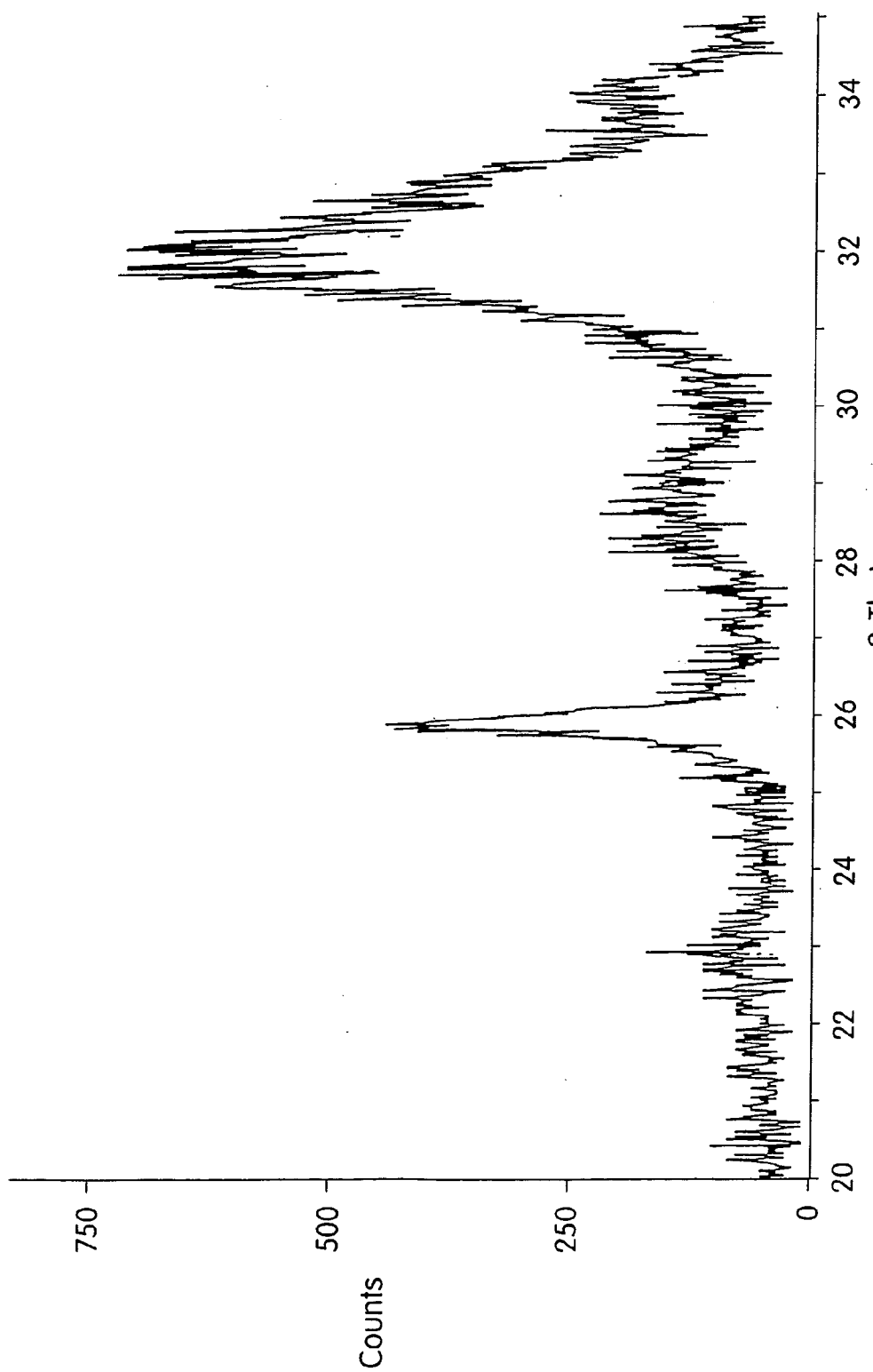
FIG. 14 is an X-ray diffraction pattern of PCA calcium phosphate prepared as described in Example 1-2.
Figure 15:
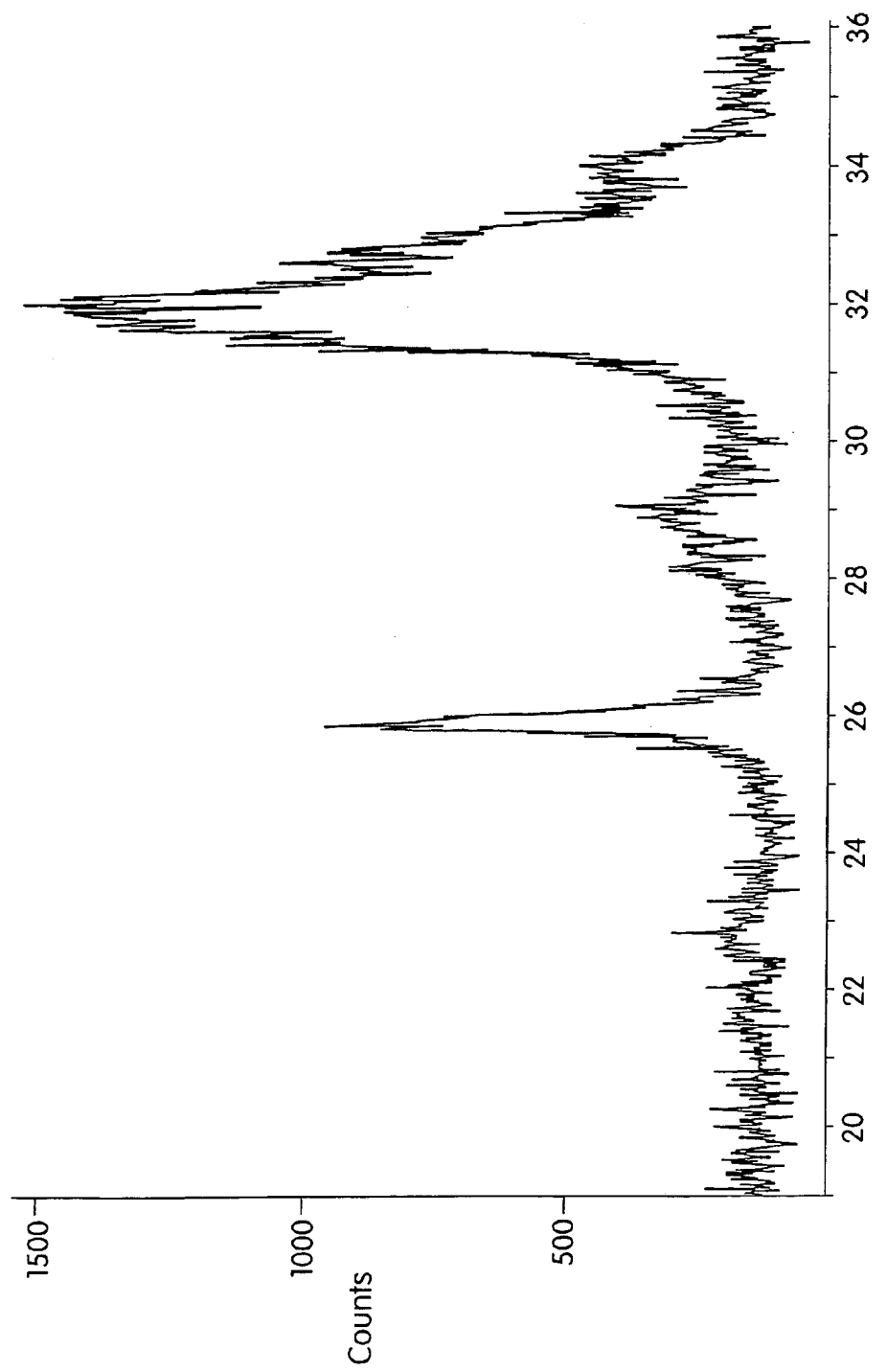
FIG. 15 is and X-ray diffraction pattern of PCA calcium phosphate prepared as described in Example 1-4.

ACP was mixed with the specific promoter at a ratio (wt/wt) of about 50:50 (See Table 1) for 5 minutes in a SPEX laboratory mill. Approximately 0.8 mL $H_2O$/g dry powders were added to the dry precursor mixture and mixed to a paste. The mixture was then shaped into a ball, wrapped in moist tissue paper and heated to 37° C. for at least 30 minutes. After 30 minutes and at various time points thereafter the paste was monitored for hardness. FIGS. 14 and 15 are representative XRD from reactions 1-2 and 1-4. The use of two different grain size hydroxyapatites as participating promoters yielded similar results as with different grain size DCPDs (see Example 10) That is, the larger grain size

TABLE 2

ACP Conversion Using Passive Promoters

| study # | Passive Promoter (ACP:promoter) | Incubation time at 37° C. | Extent of Hardening | PCA* by FTIR | PCA* by XRD |
|---|---|---|---|---|---|
| 2-1 | $SiO_2$ (5:1) | 30 min 3 hrs | soft very hard | yes | yes |

TABLE 2-continued

ACP Conversion Using Passive Promoters

| study # | Passive Promoter (ACP:promoter) | Incubation time at 37° C. | Extent of Hardening | PCA* by FTIR | PCA* by XRD |
|---|---|---|---|---|---|
| 2-2 | Mica (5:1) | 30 min | soft | yes | yes |
| | | 12 hrs | very hard | | |
| 2-3 | $Al_2O_3$ (1:1) | 30 min | soft | yes | yes |
| | | 12 hrs | very hard | | |
| 2-4 | $Al_2O_3$ (5:1) | 30 min | soft | yes | yes |
| | | 12 hrs | very hard | | |

*PCA = poorly crystalline apatitic calcium phosphate

EXAMPLE 4

This example demonstrates the use of a scanning differential calorimeter (DSC) to monitor temperature sensitivity and the net endothermic nature of a preferred embodiment reaction employing activated ACP and DCPD precursors.

Figure 16:
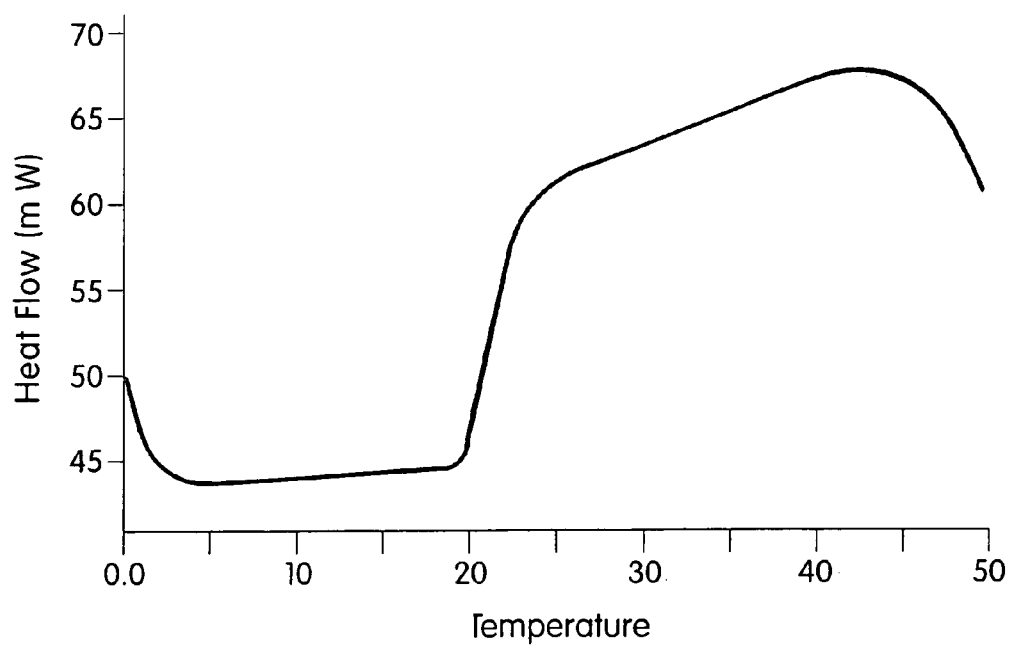
FIG. 16 is a differential scanning calorimeter (DSC) plot of the reaction of reactive ACP with DCPD showing endothermic nature of the reaction.

The dry precursor mixture containing equal weights of ACP and DCPD was prepared as described in Example 9. Water (0.05 mL), prechilled to approximately 4° C., was added to 47.27 mg of the dry precursor mixture and immediately placed into the calorimeter. The DSC (Perkin Elmer 7 series thermal analysis system) was set to a starting temperature of 0° C. with a scan rate of 5° C./min. The results are shown in FIG. 16. The plot represents a monitoring of the first 7 minutes of reactivity and shows essentially no heat flow between 0.0° C. and approximately 20° C., at which point onset of endothermic heat flow occurs. The heat flow properties indicate that at 37° C. the reaction is essentially endothermic, and under the conditions used, the reaction occurs only very slowly if at all at temperatures below about 20° C. Thus, the net reactivity in the system, that is, the sum of endothermic and exothermic heat flow of the system, is endothermic.

EXAMPLE 5

This example describes the step-by-step preparation and methods for the synthesis of a highly reactive amorphous calcium phosphate of the present invention.

The inert carbonated amorphous calcium phosphate was then prepared at room temperature by the rapid addition of solution B (43 g $Ca(NO_3)_2.4H_2O$ (calcium nitrate tetrahydrate) and 1 g $MgCl_2.6H_2O$ in 0.5 l of distilled water) to rapidly stirring solution A (55 g $Na_2HPO_4.7H_2O$ (sodium phosphate), 50 g NaOH (sodium hydroxide), 30 g $NaHCO_3$, (sodium bicarbonate) and 2 g $Na_4P_2O_7.10H_2O$, in 1.3 l of distilled water). The precipitate of gel-like amorphous calcium phosphate thus formed was immediately filtered using filter paper (0.05 sq. m) with medium filter speed and a vacuum pressure of about $10^{-2}$ torr. The material formed a thin cake and was washed with approximately 4 liters of distilled water by adding water into the filtration funnel. The washed material was then collected using spatula and immersed into a liquid nitrogen in a 2.5 L container. Following the formation of hard frozen pieces, the container was transferred into a vacuum chamber for 24 hrs ($10^{-1}$–$10^{-2}$ torr), until a fine and dry powder was obtained.

Although the procedure described above may be performed at room temperature, the entire process preferably takes place below ambient temperature (4–5° C.), so as to further prevent the amorphous state from converting into more stable crystalline form.

An infrared spectrum of the inert amorphous material at this point in process is shown in FIG. 17a. This spectrum contains peaks characteristic of P—O groups (570 and 1040 $cm^{-1}$), $CO_3^{2-}$ group (1,420$^{-1}$, 450 $cm^{-1}$) with a relatively large O—H group peak (~3,550 $cm^{-1}$). The X-ray diffraction pattern of the same material demonstrates the amorphous nature of the material as indicated by absence of any sharp peaks in the 2θ=20 to 35 range.

The amorphous material described above was then activated to the highly reactive form by heating for 60 minutes at 450° C. (±3° C.). The IR of the heated material is shown in FIG. 17b. This spectrum shows a reduction of particular O—H and $CO_3^{2-}$-groups, indicating a significant reduction of $H_2O$ and $CO_3^{2-}$ as $CO_2$ and $H_2O$. In similarly prepared samples the carbon content was observed to drop approximately 60% with a total carbonate ratio decreasing from 1.56% to 0.5%. Note, however, that the amorphous nature of the material was not lost during this process, as demonstrated by the x-ray diffraction pattern shown in FIG. 6a. The Ca/P ratio measurement of this material after the heat treatment was determined to be 1.575, using a method of quantitative electron microprobe analysis. The overall morphological and ultrastructural properties of the amorphous material was confirmed by transmission electron microscopy as shown in FIG. 1. Note the "amorphous" appearance of the material with absence of sharp edges separating each granules with certain portion of the material to exhibit shapeless form (arrows).

EXAMPLE 6

ACP was synthesized as described in Example 5 above, with the exception that solutions A and B were prepared in the following way: Solution A was prepared at room temperature by the rapid dissolution of 90.68 g of $Ca(NO_3)_2.4H_2O$ in 1.2 liter of carbonated distilled $H_2O$. Solution B was prepared by dissolving 40.57 g of $K_2HPO_4$ in 1.53 liters of distilled $H_2O$, containing 24 ml of 45 vol. % KOH solution. Chemical and physical properties of the product amorphous calcium phosphate resulting from this procedure were similar to those of the material prepared accordingly for Example 5.

EXAMPLE 7

ACP was synthesized as described in Example 5 above, with the exception that solutions A and B were prepared in the following way: Solution A was prepared at room temperature by the rapid dissolution of 10.58 g of $Ca(NO_3)_2.6H_2O$ in 0.15 liters of carbonated distilled $H_2O$ at pH greater than 9.0, as adjusted by NaOH. Solution B was prepared by dissolving 7.8 g of $(NH_4)_2HPO_4$ in 0.35 liters of distilled $H_2O$.

EXAMPLE 8

This example describes the preparation of PCA calcium phosphate of the invention with manual mixing of the dry reactants.

Dicalcium phosphate dihydrate (DCPD) was prepared at room temperature by the rapid addition of solution B (17.1 g $Ca(NO_3)_2.4H_2O$ (calcium nitrate tetrahydrate) in 250 mL distilled water) to solution A (10 g $H_9N_2O_4P$ (diammonium hydrogen phosphate) in 500 mL distilled water at a pH of 4.6–4.8) with constant stirring. Immediately thereafter, the sample was filtered using filter paper (0.05 sq. m) with medium filter speed and a vacuum pressure of about 10–2 torr. The material formed a thin cake which was washed with about 2 liters of distilled water and then dried at room temperature for 24–72 hrs.

The reactive amorphous calcium phosphate material prepared from Example 5 was physically dry-mixed with dicalcium phosphate dihydrate ($CaHPO_4 \cdot 2H_2O$) at 50:50 wt. % using a mortar and pestle for 3–5 min. Water (1 mL/g of mixed material) was then added to the powder mixture to yield a paste-like consistency. The amount of $H_2O$ added varied, depending on whether a thick or thin paste was desired. The hydrated precursor material was then wrapped loosely in moist tissue paper and heated to 37° C. At this temperature the paste hardened into a solid mass by means of a substantially endothermic reaction. The hardening process could be delayed for several hours by refrigerating the sample at 4° C. The hardened material was composed of PCA calcium phosphate with an inherent solubility property that exceeded reported solubilities for a synthetic hydroxyapatite material. This is demonstrated in FIG. 3, where the concentration of calcium ions released into a controlled pH buffer solution over 24 hrs at 37° C., was significantly higher for the PCA calcium phosphate material of the present invention (curve 50) than the standard crystalline hydroxyapatite material (curve 52).

EXAMPLE 9

This example describes the preparation of the inventive PCA calcium phosphate using automated mixing of the dry precursors.

The dry ACP and DCPD precursors were prepared as described in Example 8. Instead of mixing with a mortar and pestle, the ACP and DCPD were mixed using a SPEX 8510 laboratory mill with a SPEX 8505 alumina ceramic grinding chamber for 2 min. Preparation of the hydrated precursor was accomplished by adding from 0.7 to 1.5 mL of water per gram of mixed dry precursors.

EXAMPLE 10

This example demonstrates the preparation of PCA calcium phosphate using DCPDs of specific grain size distributions.

Figure 8:
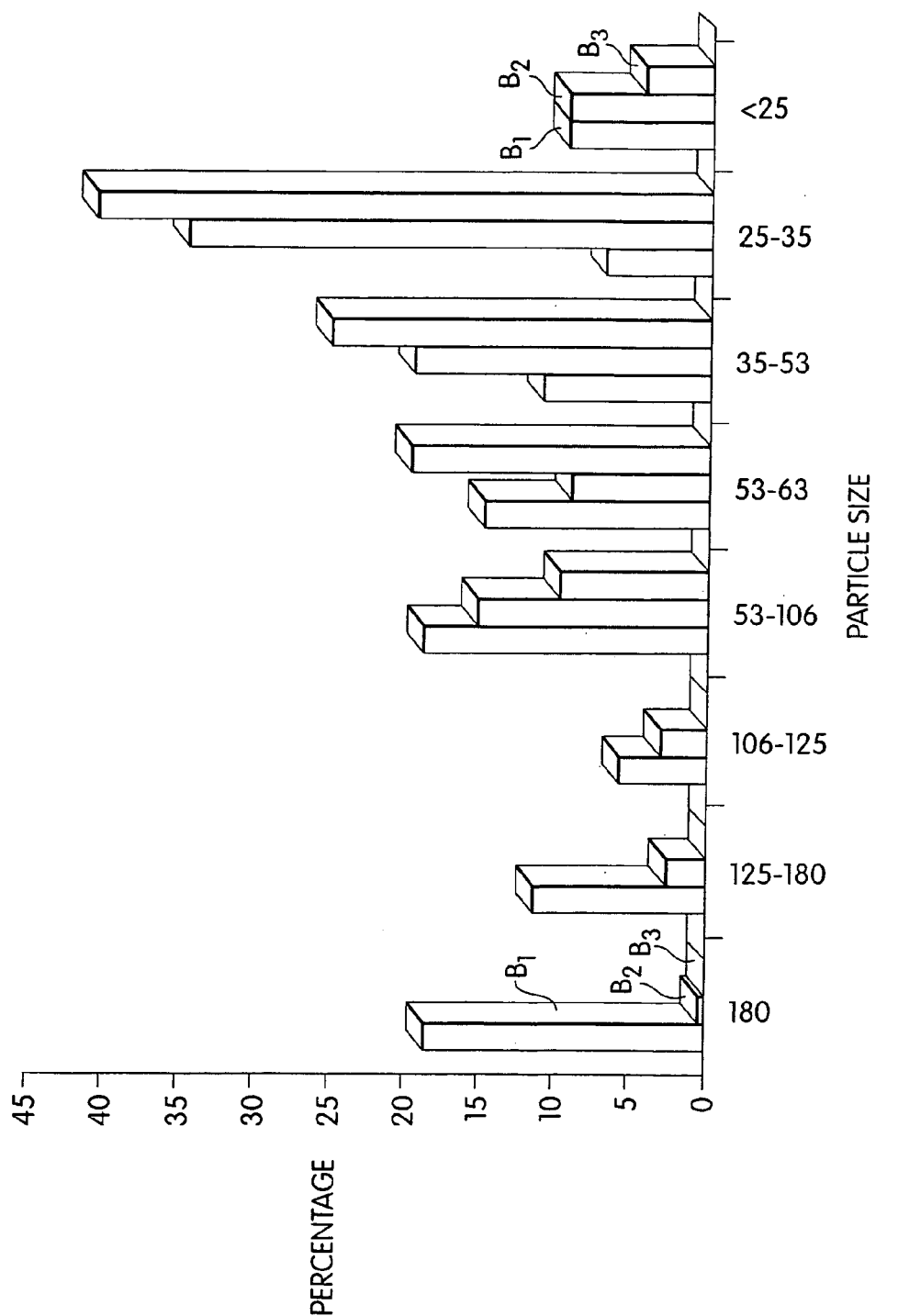
FIG. 8 is a bar graph displaying particle size distribution for various formulations described in Example 10.

DCPD was prepared as described in Example 8. The dry material was ground for 5 minutes in a SPEX 8510 laboratory mill with a SPEX 8505 alumina ceramic grinding chamber. Following grinding, the material was serially sieved through a Tyler test sieve shaker to produce DCPD with 8 different grain size distributions as indicated in Table 3 and shown in FIG. 8.

TABLE 3

DCPD Grain Size Distribution

| Sample | Grain Size Distribution | Extent of hardening at 30 min, 37° C. |
|---|---|---|
| 10-1 | <25 μm | hard |
| 10-2 | 25–35 μm | hard |
| 10-3 | 35–53 μm | hard |
| 10-4 | 53–63 μm | hard |
| 10-5 | distribution B3 (FIG. 8) | hard |
| 10-6 | 106–125 μm | not fully hardened |
| 10-7 | distribution B2 (FIG. 8) | not fully hardened |
| 10-8 | unsieved distribution B1 (FIG. 8) | not fully hardened |

It has been found that the preliminary grinding of DCPD prior to sieving can be replaced by a brief hand grinding using a mortar and pestle without substantially changing the results.

The reactive amorphous calcium phosphate material prepared from Example 5 was physically dry-mixed 1:1 (wt/wt) with each of the DCPD samples from Table 3 for 10 minutes using a SPEX 8510 laboratory mill with a SPEX 8505 alumina ceramic grinding chamber. Water (0.8–1.0 mL/g of dry mix) was then added to each powder mixture to yield a hydrated PCA calcium phosphate precursor with a paste-like consistency. Six of the eight samples indicated in Table 3 hardened well in 30 minutes at 37° C. Samples 10-6, 10-7 and 10-8 did not harden as quickly or as firmly as the other samples. Each of these samples had significantly higher percentages of >100 μm particles than the other samples. It is concluded from these observations that the use of smaller grain size DCPD leads to more rapid and complete hardening than larger grain size DCPD.

EXAMPLE 11

This example describes two preferred embodiments of the instant invention.

(a) Reactive amorphous calcium phosphate material prepared according to Example 5 was physically dry-mixed with DCPD with a particle size distribution of B3 of FIG. 3 at 50:50 wt. % using a SPEX 8510 laboratory mill for 2 min with a SPEX 8505 alumina ceramic grinding chamber, followed by sieving to a size of less than 150 μm. Water (0.8 mL/g of mixed material) was then added to the powder mixture to from the hydrated precursor.

(b) This preferred embodiment was prepared as in (a) with the exception that samples were dry mixed and subsequently ground for 10 minutes.

EXAMPLE 12

This example describes alternative methods for preparing hydrated PCA calcium phosphate precursor.

(a) Reactive ACP and DCPD were prepared as described in Example 9 with the exception that the dry precursors were not mixed. Water (0.8 mL) was added to ACP (0.5 g) and mixed thoroughly to homogeneity with a spatula to form a paste. DCPD (0.5 g) was then added to the paste and the paste was mixed for approximately 2 min. The resultant paste was placed into a moist environment at 37° C. for 30 min.

(b) Reactive ACP and DCPD were prepared as described in Example 8. Water (0.8 mL) was added to DCPD (0.5 g) and mixed thoroughly to homogeneity with a spatula to form a paste. ACP (0.5 g) was then added to the paste and the paste was mixed for an additional 2 min. The resultant paste was placed into a moist environment at 37° C. for 30 min.

In both instances, the paste hardened after 30 minutes, indicating a successful reaction.

EXAMPLE 13

This example describes hardness testing of a PCA calcium phosphate calcium phosphate.

PCA calcium phosphate calcium phosphate was prepared according to Example 9 to form a paste. The paste was placed into a 6 (dia.)×10 (depth) mm hollow teflon tube submersed in 37° C. water for 30 minutes. The hardened PCA calcium phosphate was then removed from the tube and placed in water at 37° C. for 1 hour and then, while still moist, placed vertically on an Instron 4206 having a dual 10 kg/15 ton load cell. Compressibility was determined using a crush test. Approximately, 200–250 N were required to bring the sample to failure. This force corresponds to a compressive strength of 7–9 MPa.

EXAMPLE 14

These examples demonstrate the effect of fluid volume on the consistency and reactivity of injectable paste to be used in the formation of bone substitute material. Each of the pastes were prepared as described in Example 8, above, and the consistency and rate of reaction at room temperature and 37° C. were determined. Observations are reported in Table 4.

TABLE 4

Formability, Injectability and Reactivity of Hydrate Precursor.

| Example No. | water volume (mL) | formability | inject-ability | hardening time at various temps. (4° C./RT/37° C.) |
|---|---|---|---|---|
| 14-1 | 0.7 | — crumbles | — | —/—/— |
| 14-2 | 0.8* | +++ easily formed paste | + | >60 min/>60 min/30 min |
| 14-3 | 0.9* | ++ toothpaste | ++ | >60 min/>60 min/30 min |
| 14-4 | 1.0 | + liquid toothpaste | +++ | >60 min/>60 min/30 min |

*Under some circumstances (e.g., evaporation) these samples may dry out somewhat over a period of one hour at room temperature. In such cases, additional water may be added to restore the original consistency.

EXAMPLE 15

Implantation and Resorption of PCA calcium phosphate in a Subcutaneous Site. This example demonstrates the resorption of the inventive PCA calcium phosphate when implanted subcutaneously into rats. It also demonstrates a useful screening procedure to test resorption characteristics of new formulations of bioceramic implant materials and composites.

Eighty male and eighty female Sprague-Dawley rats were each implanted with 4 ml (2–4 gm) of the inventive PCA (prepared according to Example 8) into the dorsal subcutis (>10×the amount considered maximal in humans on a per kg basis). Control animals were treated with an equal volume of saline. Operation procedures are described in Example 16. The rats were sacrificed according to the schedule presented below in Table 5; the implant site was examined as described in Example 16.

TABLE 5

| Sacrifice Schedule | |
|---|---|
| Sacrifice Timepoint | PCA calcium phosphate implant |
| 1 week | 5 m/5 f |
| 2 weeks | 5 m/5 f |
| 1 month | 5 m/5 f |
| 3 months | 5 m/5 f |
| 1 year | 20 m/20 f |

Blood for clinical pathology analyses was collected via retroorbital sinus or cardiac puncture (all by the same method) while the animals were under $CO_2$ anesthesia. Blood samples were collected from each group of animals prior to scheduled sacrifice. Clinical observations of the animals for general health and well-being were performed at least weekly until 3 months, and then monthly.

At 1 week PCA material was present at the implant site and was found associated with moderate to marked granulomas presumable associated with the resorption process. At week two a small amount of PCA material was still present at the implant site and associated granulomas were mild to moderate. By week four most tissue appeared normal with a few mild granulomas persisting at the implant site. At week twelve no evidence of the implant remained.

EXAMPLE 16

Implantation and Resorption of PCA calcium phosphate in an Intramuscular Site. This example describes the preparation of PCA calcium phosphates that have varied in vivo resorption times as a result of varied grinding times.

Individual dry precursors, ACP and DCPD were prepared as described in Example 8. Several different formulations of DCPD and ACP were then prepared by i) grinding DCPD for 15 sec, 30 sec, 1 min, 2.5 min, or 5 min in a SPEX grinder; ii) combining the ground DCPD 1:1 with ACP; and iii) grinding the mixture for an additional 15 sec, 30 sec, 1 min, 2.5 min, or 5 min, respectively. Total grinding times for the different preparations were therefore 30 sec, 1 min, 2 min ("Type 2" powders), 5 min, and 10 min ("Type 10" powders).

The PCA calcium phosphate, sterilized in powder form by approximately 2.5 Mrad of gamma irradiation, was prepared as described in Example 4 by taking the material in powder form and mixing with sterile water or saline and forming it into approximately 1 cm disks 2 mm thick and incubated for a minimum of 30 minutes at 37° C. Disks were implanted into adult male New Zealand White Rabbits immediately following fabrication.

Animals were assigned to dose groups which contained 3 males for a total of 15 animals. The implants were assigned to the rabbits randomly. 10–15 minutes prior to the surgery, the animal was premedicated with xylazine (10 mg/kg, i.m.). The animal was then given ketamine (50 mg/kg, i.m.). The dorsal surface of the animal was clipped free of hair and washed with a betadine surgical solution and alcohol. Before the surgery the animal was monitored to be sure that is was properly anesthetized. To do this, pressure was applied to the foot pad. When there was no response, the animal was properly anesthetized. Throughout the procedure, the animal was monitored for whisker twitching and the toe-pinch reflect, which indicated that the animal was not waking up.

Using aseptic technique and a scalpel blade, an incision 1–2 cm in length was made in the skin over the m. longissimus lumborum (which lies along both sides of the spine). When the incision was made, the underlying fascia and muscle was also cut to allow the sample to pas into the muscle. The sample disk was placed directly into the muscle, being sure that the entire implant was embedded in the muscle. The muscle was closed with a single absorbable suture and the skin was stitched closed subcutaneously. Metal skin staples were used to close the external skin surface incision. Five samples were placed on each side in this manner. Each sample was placed at the end of the incision and they were approximately 1 cm apart from each other (see diagram). The samples were in the form of 7 mm by 2 mm disks weighing approximately 150 mg. The animals were monitored and were given buprenorphine (0.02–0.05 mg/kg, s.q) upon awakening. The analgesic was administered 2 times per day for three days after surgery.

The animals were radiographed immediately after the surgery and for every two weeks thereafter. The radiographs were compared to track the resorption of the materials. A standardized method was used for the radiographs to minimize any variation between timepoints.

After euthanasia, implant sites were first evaluated by gross examination. In those sites with visible implants, the implants appeared as grey to yellow solid discs. In those sites where the implant had been resorbed, areas of red to tan discoloration of the muscle were observed.

Muscle tissue, with the implants, was removed, being careful not to disturb the implants. The tissues and the identifying marks were placed into labeled jars filled with 10% neutral buffered formalin. All implant sites were processed and evaluated microscopically. Observations included focal fibrosis, focal granulomatous inflammation, and appearance of the implant (in some cases). Fibrosis was primarily seen as fibrocytes and collagen. Animals with gross resorption had fibrosis and minimal to moderate granulomatous focal inflammation. Granulomatous inflammation was seen as focal aggregates of macrophages and giant cells, often with intracytoplasmic crystals, and occasional heterophils and lymphocytes. Inflammation around the non-resorbed implants was primarily minimal to mild fibrosis and/or granulomatous inflammation, both of which are within the acceptable range for intramuscular implants.

At four weeks, the pellets made from PCA calcium phosphate implants that had been prepared by grinding for 30 seconds, 1 minute, or 2 minutes were fully resorbed. Those that had been prepared by grinding for 5 minutes or 10 minutes were not fully resorbed.

EXAMPLE 17

Reactive amorphous calcium phosphate material is prepared as Example 5 and is dry-mixed with other calcium phosphate compounds, according to the method described in Example 8 with the following modification. Instead of DCPD, the following calcium phosphate compounds are used, including, but not limited to: $Ca(PO_3)_2$ (calcium metaphosphates), $Ca_7(P_5O_{16})_2$ (heptacalcium phosphate), $Ca_2P_2O_7$ (calcium pyrophosphate), $Ca_3(PO_4)_2$ (tricalcium phosphates). The dry-mixture ratio is properly calculated to be between Ca/P ratios of 1.5–1.70, depending on the molar Ca/P ratio of the compound mixed with the reactive amorphous calcium. The PCA calcium phosphate identity of the resulting material is then confirmed through the use of XRD and FTIR.

EXAMPLE 18

This example follows the conversion reaction occurring in association with the hardening of the hydrated precursor using X-ray diffraction and Fourier transform infrared spectrometry.

Hydrated precursor was prepared as described in Example 9. The reaction mixture was placed in a moist environment at 37° C. and examined by X-ray diffraction spectrometry at different times. FIGS. 5*a*–*d* are the X-ray diffraction spectra of the reaction product between DCPD and the reactive amorphous calcium phosphate as described in Example 5. X-ray scan conditions are (a) copper anode, (b) λ=1.4540598, and (c) a scan range 20–35° at a step of 0.02° and step interval of 2 seconds. FIG. 6 shows the infrared spectra of dicalcium phosphate dihydrate (FIG. 6*a*), the activated ACP of the invention (FIG. 6*b*), and the poorly crystalline hydroxyapatite of the present invention (FIG. 6*c*).

Figure 4B:
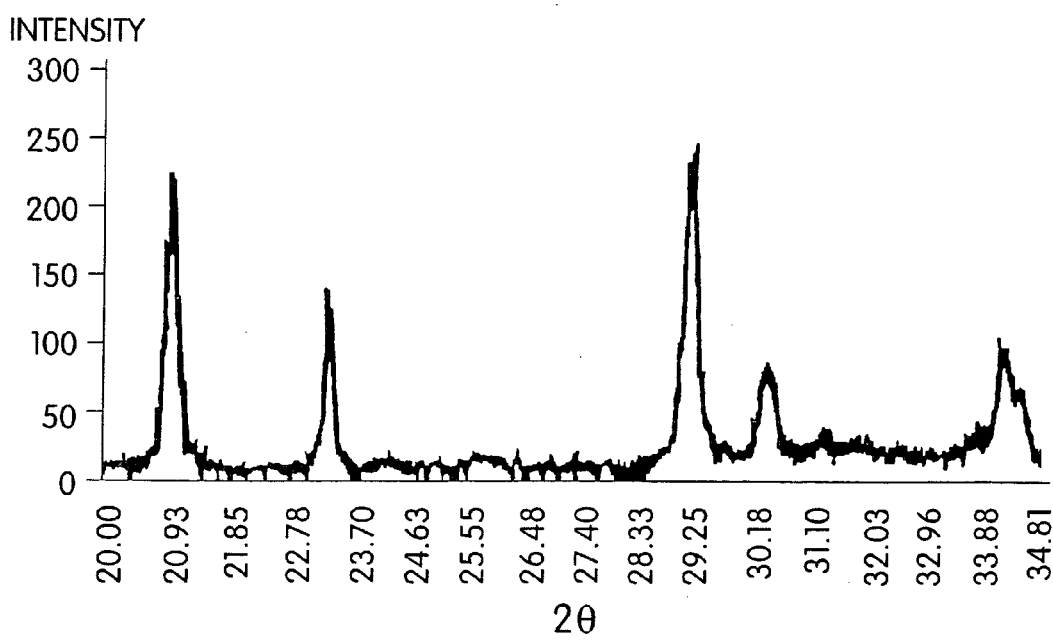
Figure 5A:
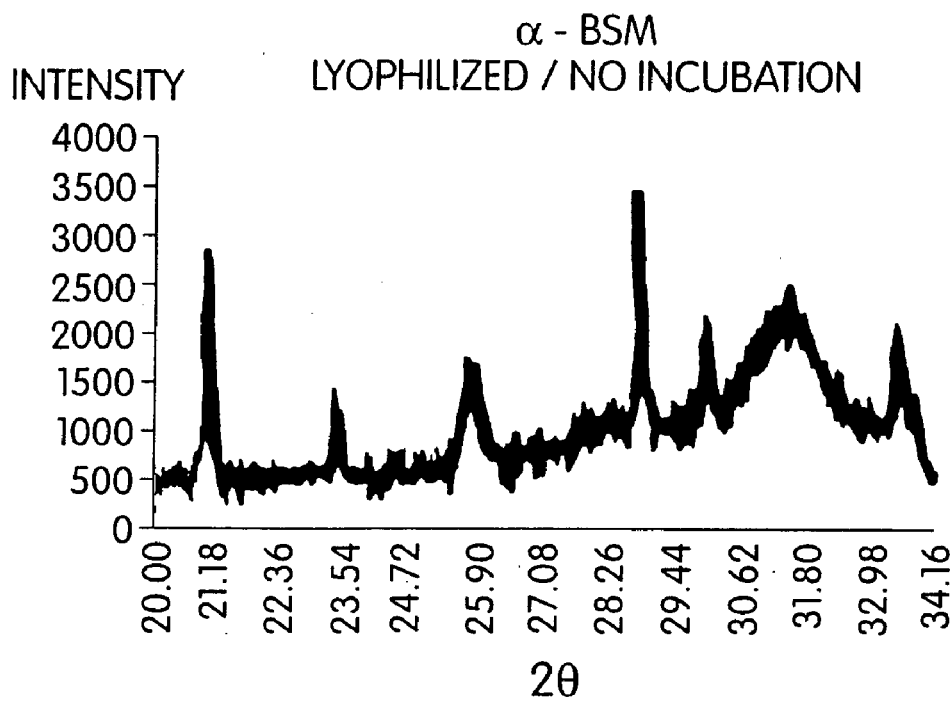
FIGS. 5a–d are X-ray diffraction patterns tracking the progress of the reaction of a mixture of reactive amorphous calcium phosphate and dicalcium diphosphate to form a PCA material of the present invention.
Figure 5B:
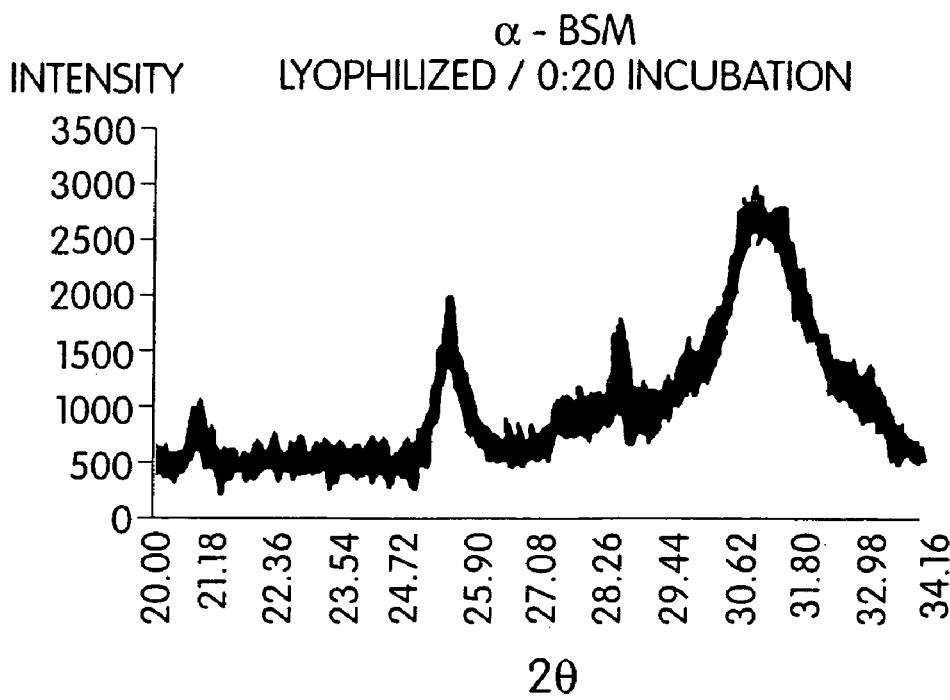
Figure 5C:
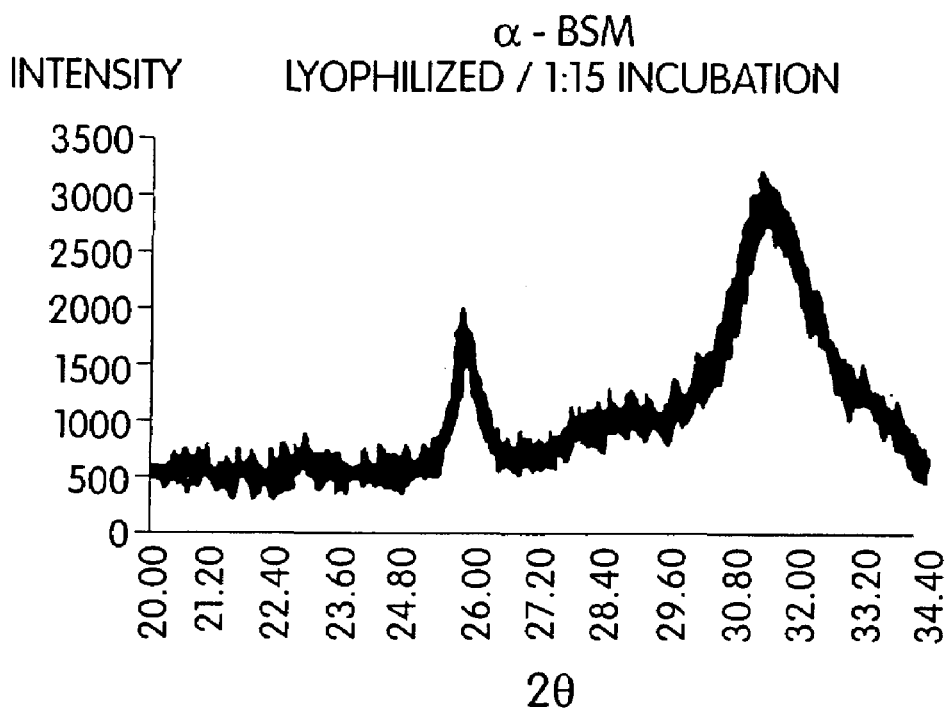
Figure 5D:
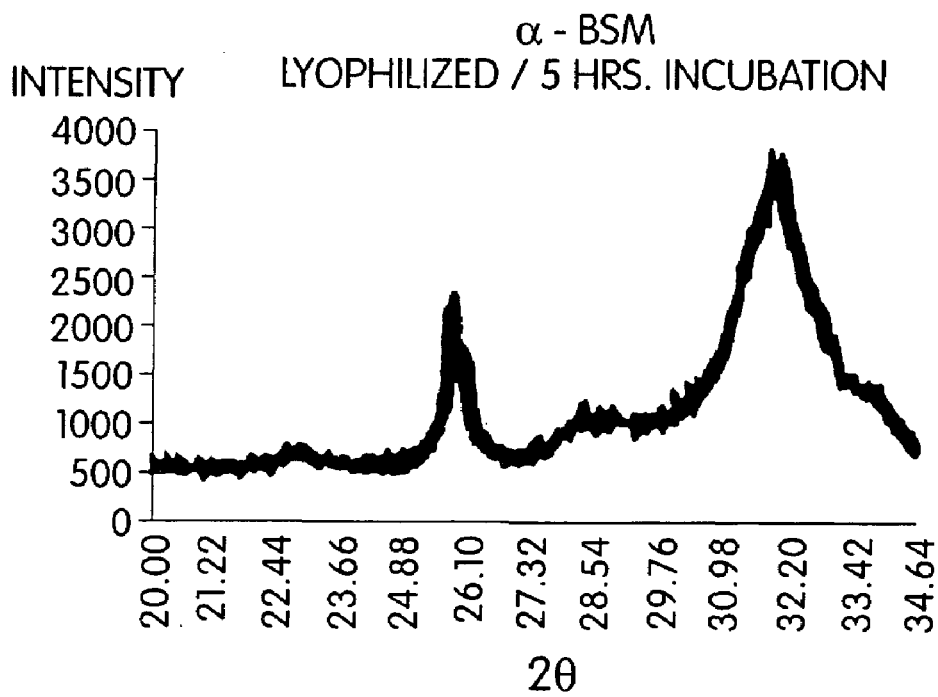
Figure 6A:
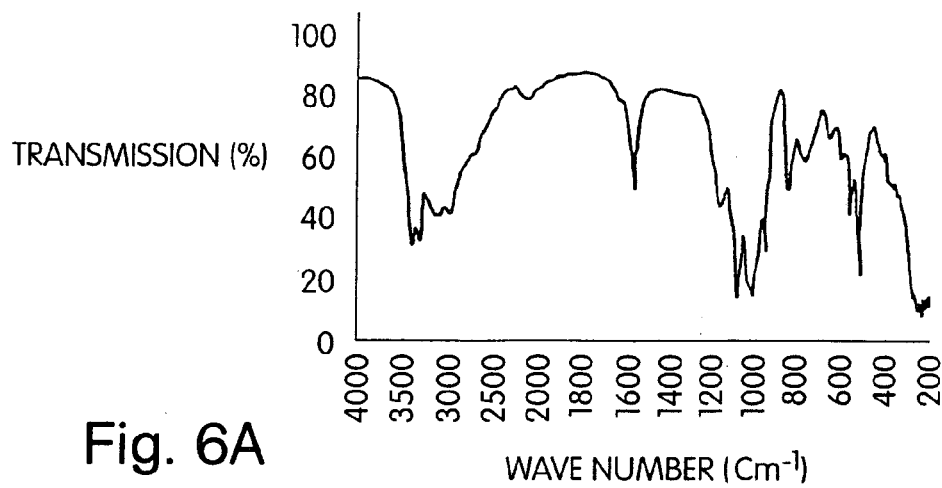
FIG. 6 is infrared spectra of (a) dicalcium phosphate dihydrate, (b) the activated ACP of the invention, and (c) the PCA material of the present invention.
Figure 6B:
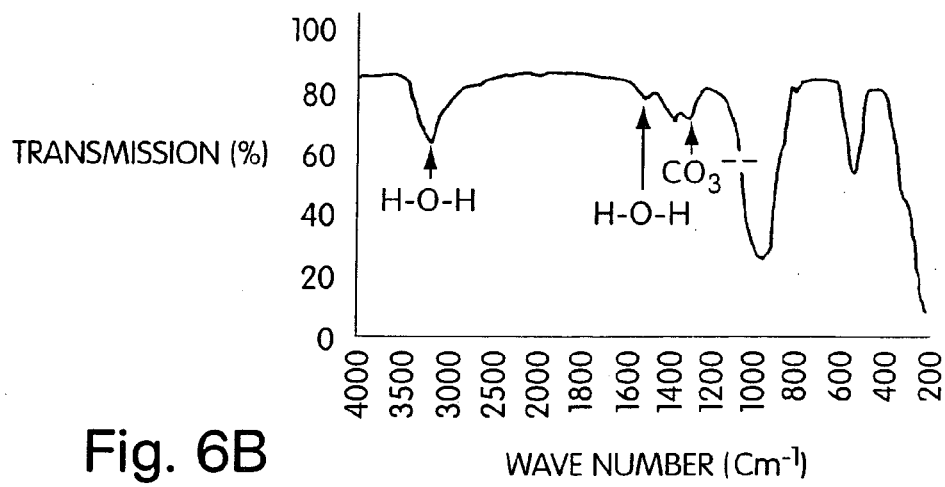
Figure 6C:
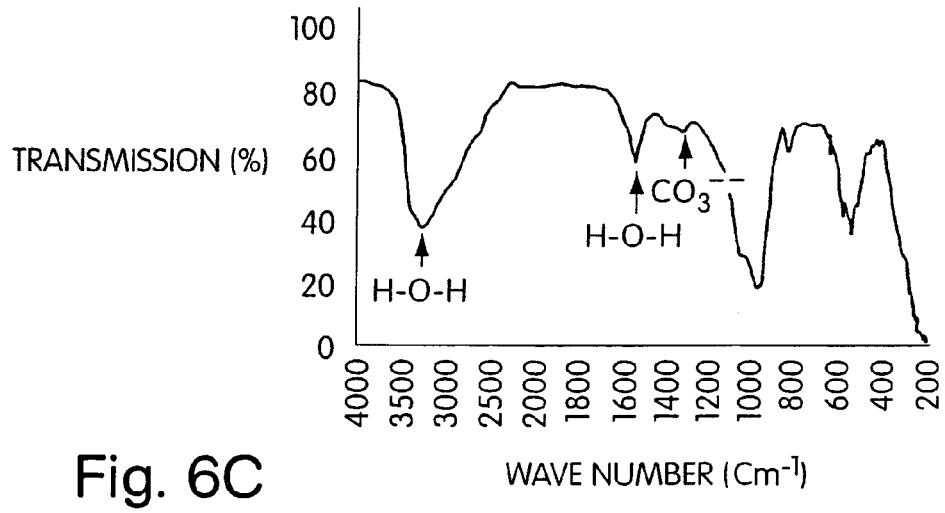
Figure 7:
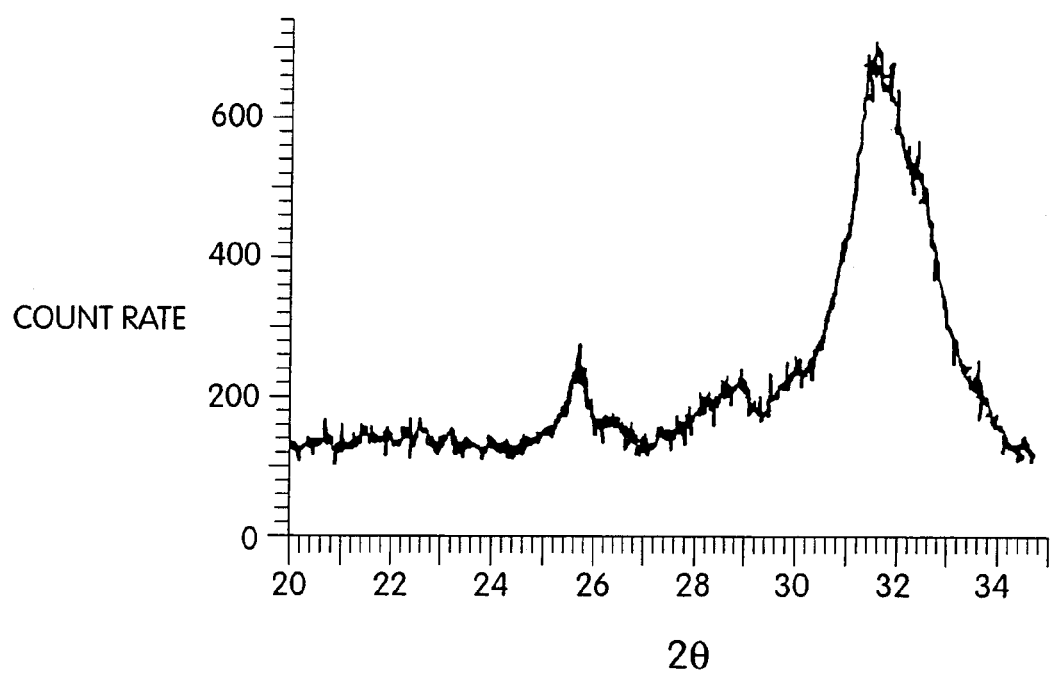
FIG. 7 is an X-ray diffraction pattern of naturally occurring bone.

Samples shown in FIGS. 5*a*–5*d* were incubated for 0, 20 min, 75 min and 5 hours, respectively. The samples were removed at the noted time and lyophilized to preserve chemical characteristics. FIG. 5*a*, taken at the start of the reaction, represents a combination of peaks attributable to the starting ACP and dicalcium diphosphate (see, FIG. 4 for component XRD patterns). The sharp peaks at ca. 20.25°, 23.5°, 29.5°, 30.75° and 34.2° for crystalline dicalcium diphosphate are readily observed. With increasing reaction time, the sharp crystalline peaks subside and wide (amorphous) peaks appear centered at 2θ=26°, 28.5°, 32.0° and 33.0°. It is interesting to note that there is no change in the spectra after 75 minutes of reaction, indicating that the reaction essentially complete in little more than one hour. The X-ray diffraction pattern of the bone substitute material of the invention (FIG. 5*d*) can be compared to that of naturally occurring bone, shown in FIG. 7. The two spectra are nearly identical.

EXAMPLE 19

Implantation and Resorption of PCA calcium phosphate in a Bony Site

The purpose of this study was to assay resorption and ossification of PCA calcium phosphate in a bony implant site. The method is also useful for testing the resorption and ossification properties of PCA calcium phosphate formulations and composites of the invention.

The test article used was a PCA calcium phosphate formulation prepared as described in Example 4. The ACP and DCPD were mixed in the specified proportions and ground for 1 minute, 30 seconds in the SPEX grinder equipment.

Adult (>5 month old) NZW male rabbits were held in quarantine and acclimatized for a minimum of 10 days prior to the initiation of the study. Animals were individually housed in suspended stainless steel cages. Wood shavings were used in dropping pans under the cages. Prior to initiation of the study, animals were assigned to groups or treatments randomly and were identified by a numbered ear tattoo and by a corresponding cage card. All animals had single defects placed in one tibia. Timepoints for evaluations were 2, 4, and 8 weeks (2 animals at each timepoint). Surgery was performed under full anesthesia and aseptic surgical conditions.

After obtaining adequate anesthesia (e.g., ketamine/xylazine to effect), using aseptic technique, an incision was made over the lateral proximal tibia. The soft tissue was deflected away and the bone exposed. Using an approximately 5 mm trephine in a low speed dental handpiece with irrigation (0.9% physiologic saline) as needed, a ~5.5 mm diameter hole was cut through the cortical portion of the bone. The bony disk was dissected free from the cortex and the site was prepared for implantation. The hydrated precursor material in paste form was placed into the defect. Defects in control animals were left untreated. The soft tissues were then closed in layers. One sample per animal was prepared using this method.

Clinical observations of the animals' general health and well-being, with special regard to their ambulatory abilities, were made at least weekly. All animals appeared to be in good health. At the end of the study the animals were euthanized with an overdose of anesthetic and the implant site collected. Radiographs of the tibiae were made at scheduled intervals including after surgery and at the time of necropsy.

The implantation sites were fixed in formalin and stained with either hematoxylin and eosin, Masson's trichrome, or Von Kossa stained slides from decalcified samples. Undecalcified histological samples were also prepared and stained with light green basic fuschin. Slides were microscopically evaluated by a board certified veterinary pathologist (ACVP) with experience in laboratory animal pathology. Subjective observations were made of bone morphology, and presence or absence of organized bone and of detectable PCA calcium phosphate material was noted.

Figure 9A:
in FIG. 9a, the small arrows indicate one edge of the defect; the large arrowhead is at the yet unbridged defect.
Figure 9B:
in FIG. 9b, large arrowheads denote one edge of the defect; and in both Figures, magnification is 4×, bone is decalcified, and slides are treated with hematoxylin and eosin.
Figure 10:
FIG. 10 is a photomicrograph of canine trabecular bone grown into a defect treated with the PCA material of the present invention (magnification 10×; decalcified; hematoxylin and eosin)
Figure 11:
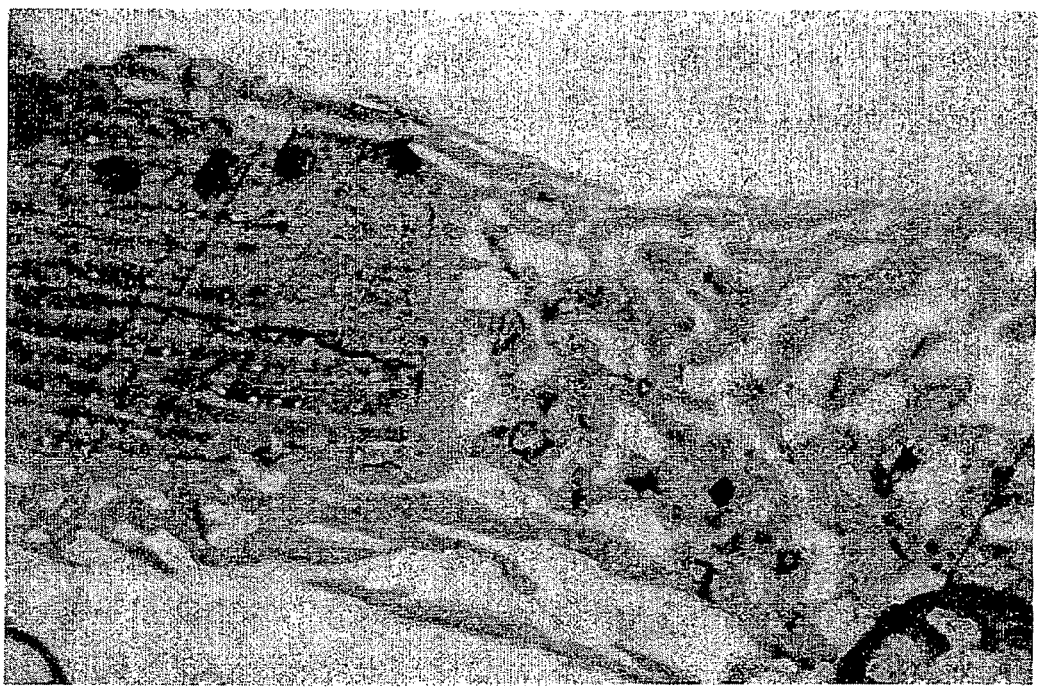
FIG. 11 is a photomicrograph of a canine cortical bone defect that was treated with the PCA material of the present invention (magnification 4×; undecalcified, Light Green Basic Fuchsin)
Figure 12A:
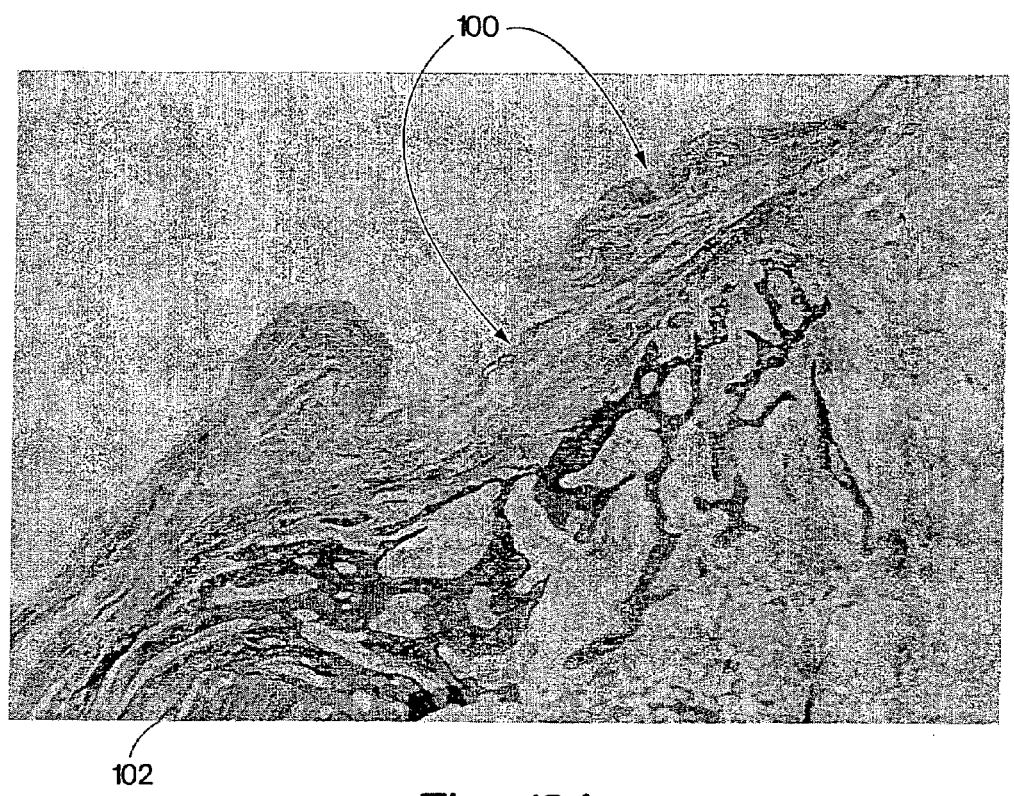
FIG. 12 presents photomicrographs of untreated (FIG. 12a) and treated (FIG. 12b) rabbit tibia defects 4 weeks after surgery (magnification 4×; decalcified; Masson's Trichrome)
Figure 12B:
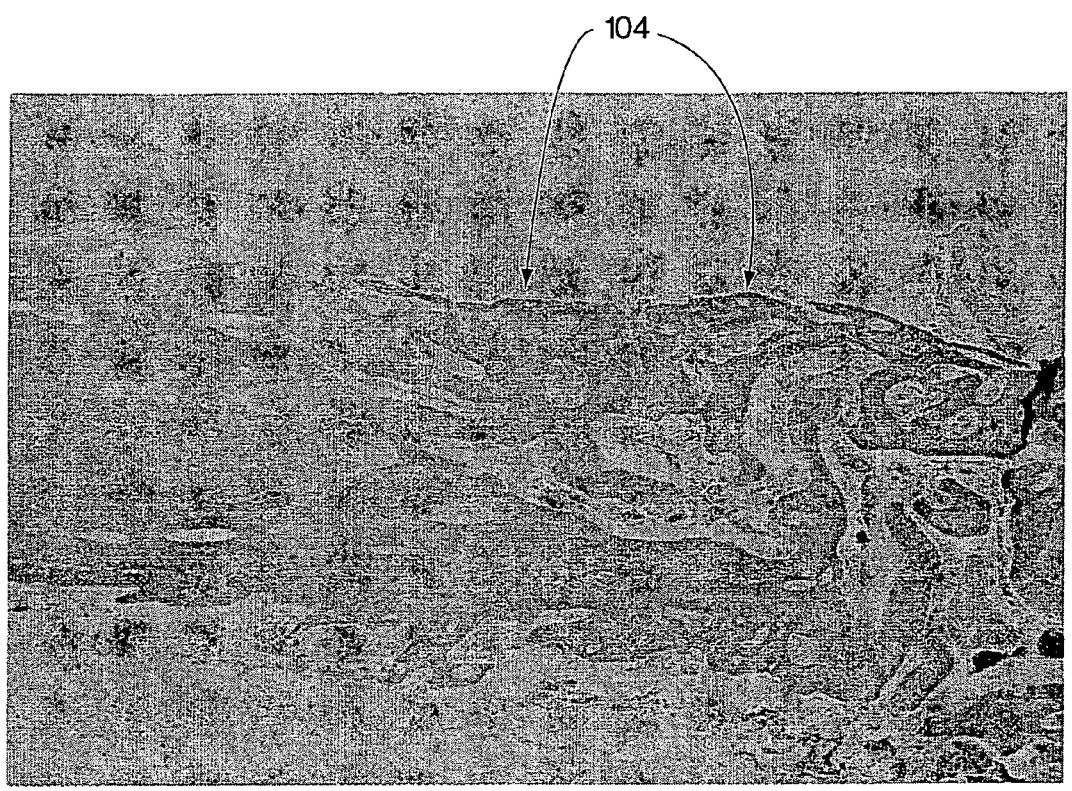

Histological results indicated some mineralization at 2 weeks. By 4–6 weeks, animals receiving implants had normal trabecular bone at the implant site with no evidence of remaining PCA calcium phosphate. The untreated controls had not fully healed in that they had less than full ingrowth and/or had non-cortical-type bone. FIGS. 9a and 9b are photomicrographs of untreated and treated tibia defects, respectively, 2 weeks after surgery. As can be seen, bone to the right of the defect edge in the untreated sample (FIG. 9a) is thin trabecular bone; new bone to the right of the defect edge in the treated sample (FIG. 9b) is thick trabecular bone.

EXAMPLE 20

This example demonstrates the difference in resorption time between two precursor formulations with different DCPD grain size distributions. PCA calcium phosphate precursor material is prepared according to example 10. Two precursor mixes are prepared. Sample A corresponds to sample 10-6 and sample B corresponds to a 2:4:3:1 mix of samples 10-1, 10-2, 10-3 and 10-4. Hydrated precursor pastes of the two samples are tested in rodents in the subcutaneous test of example 15. Resorption is monitored at various time points.

EXAMPLE 21

This example demonstrates the difference in promoting activity of DCPD of two different grain size distributions in the conversion of both highly reactive and reactive ACPs ACP was prepared as in Example 5, with the exception that for some of the samples the final heat activation step was omitted. Two samples of DCPD with grain size distributions corresponding to B1 & B3 of example 10 were prepared. The ACPs and DCPDs are then mixed for 5 minutes, either by hand or in the SPEX grinder. Hardening characteristics are then determined. It is clear that machine milled samples exhibited superior hardening properties over hand ground samples. It is also clear that the samples with a smaller particle size (B3) exhibited superior hardening properties over larger grained samples (B1).

TABLE 6

Reactions Using Different Strength Promoters

| ACP | DCPD | GRINDING | HARDENING @ 30 min |
|---|---|---|---|
| heated | B3 | mortar | ++ |
| non-heated | B3 | & | (not done) |
| heated | B1 | pestle | +/− |
| non-heated | B1 |  | − |
| heated | B3 | SPEX | +++ |
| non-heated | B3 | 5–10 min | +++ |
| heated | B1 |  | + |
| non-heated | B1 |  | (not done) |

EXAMPLE 22

This example determines the specific surface area and porosity of a PCA calcium phosphate material.

ACP was prepared according to Example 5. Samples from before and after the final heat activation step were compared for their reactivity in an in vitro hardening assay with unsieved DCPD (as described in example 8). Specific surface area and average porosity were also measured. Results are tabularized in Table 7 below.

TABLE 7

Specific surface Area and Porosity of the Inventive ACPs

| sample | specific surface area (sq.m./g) | Average Porosity (Å) | DCPD Reactivity |
|---|---|---|---|
| Pre heating | 120.5 | 130 | − |
| After heating | 76.8 | 129 | + |

EXAMPLE 23

This example describes the conversion of ACP to PCA calcium phosphate in the absence of a promoter and demonstrates the failure of the newly formed PCA calcium phosphate to harden. Likewise, promoter DCPD fails to harden or convert on its own.

DCPD and a variety of ACPs and other calcium phosphates were mixed with water and tested for their ability to harden at 37° C. Table 8 summarizes these results, as well as identification of the reaction products, if any, following the test period. Under no circumstances was hardening observed up to 3 days. It was concluded that while conversion of ACP to PCA calcium phosphate may occur, the presence of a promoter is desired to achieve setting and hardening

TABLE 8

ACP conversion in the absence of a promoter

| ACP | $H_2O$ (g) | Incubation | Hardening | FTIR | XRD |
|---|---|---|---|---|---|
| ACP (Example 5) | 0.8 | 30 min | soft | ACP | ACP |
|  |  | 12 hrs | soft | PCA* | PCA* |
| DCPD (Example 8) | 0.7 | 30 min | soft | DCPD | ND |
| 38–53 μm |  | 12 hrs | soft | DCPD |  |

TABLE 8-continued

ACP conversion in the absence of a promoter

| ACP | $H_2O$ (g) | Incubation | Hardening | FTIR | XRD |
|---|---|---|---|---|---|
| ACP (Example 7) not heat activated | 1.5 | 30 min 12 hrs | soft soft | PCA* HA | ND |
| ACP (Example 5) non-carbonated | 1.5 | 30 min | soft | ACP | ND |
| ACP (Example 6) not heat activated | 1.5 | 30 min | soft | ACP | ND |
| ACP (Example 5) non-carbonated; heat activated | 1.5 | 30 min | soft | PCA* | ND |

*PCA = poorly crystalline apatitic calcium phosphate
ND = analysis not done

EXAMPLE 24

Different Hydrating Agents Effects on Hardening and Final Product.

A hydrated precursor (ACP and DCPD) was prepared as described in Examples 8, 9, or 10, with the exception that a variety of hydration media were used. Samples were then tested for hardness and completeness of reaction at various time points. In all cases, 1 g of the mixed precursors were hydrated with 0.75–1.0 mL of hydration medium to produce a paste. Table 9 summarizes the results and demonstrates that a variety of aqueous based liquids, and in particularly physiologically acceptable media, may be used in the preparation of PCA calcium phosphate.

TABLE 9

Effect of Hydrating Agents

| Hydration Medium | Incubation Time | Hardening |
|---|---|---|
| Tris | 30 min | hard |
| 0.9M NaCl | 30 min | hard |
| MEM | 30 min | hard |
| MOPS | 30 min | hard |
| HEPES | 30 min | hard |
| BUFFERALL | 30 min | hard |
| PBS | 30 min | hard |

EXAMPLE 25

ACP was prepared as described in Example 5, with the exception that the heating the ACP to 450° C. was carried out for either 1 hour or 6 hours. Following heating the ACP was prepared for reaction with DCPD as described in Example 8. Hydrated PCA calcium phosphate precursor prepared with ACP heated for 6 hours was found not to harden after 2 hrs at 37° C.

EXAMPLE 26

The porosity of a hardened sample of PCA calcium phosphate prepared according to Example 10-5 was determined.

A hardened sample of PCA calcium phosphate (1 g) was weighed immediately after removal from the moist incubator, and then air dried at room temperature for 12 hrs. The dried sample was carefully weighed and then the volume was calculated. The sample was placed into a 20 mL sample of water. After 1 minute the approximate displacement volume was noted. The dried sample was found to absorb up to 50–60% of its dry weight in $H_2O$. These results are interpreted to mean that the sample is up to 50–60% porous. Density was approximated at 1.65 g/cm$^3$.

EXAMPLE 27

This example demonstrates the use of a resorbable polymer to promote the conversion of ACP to PCA calcium phosphate.

Granular PLLA is prepared and sieved to a size of 100 μm. The powder thus obtained is mixed with the ACP (5:1 ACP:PLLA) of Example 9 and ground for 5 minutes in a SPEX laboratory mill. Water is added to 1 g of the mixture to form a workable paste. The paste is shaped into a ball and is heated to 37° C. in a moist environment for 1 hour. The hardened sample is analyzed using FTIR and XRD.

EXAMPLE 28

This example investigates the hardening characteristics of the hydrated precursor at sub-ambient temperatures.

Hydrated precursor was prepared with water as described in Example 9 and then tightly sealed to avoid evaporative loss either in parafilm or in an aluminum tube. The samples were then held for up to 1 hr, 24 hrs and 6 days. At the indicated time points, the hydrated sample was removed from refrigeration placed in a moist environment at 37° C. In all instances the samples hardened within 30 minutes.

EXAMPLE 29

This example demonstrates the efficacy of the inventive PCA calcium phosphate in promoting the healing in a large animal model, of a full segmental defect in a weight bearing limb.

Hydrated precursors Type 2 and Type 10 were prepared and treated immediately prior to surgery as described in Example 16.

Animals fasted for 24 hours prior to anesthesia, during this time interval water was available ad libitum. Ketamin (Aescoket®, 10 mg/kg i.m.) and atropine (1.5 mg i.m.) was administered as a pre-medication about 15 minutes before fully anesthetizing the animals. Etomidate (Hypnomidaat®, 0.3 mg/kg i.v.) was used as the anesthetic. After intubation, anesthesia was maintained with an $O_2/N_2O$-mixture (1:1, vol/vol) supplemented with 2% isoflurane.

Surgery was performed aseptically under full anesthesia. After shaving and iodinating the skin, an incision was made over the anteromedial side of the tibia. The muscles were bluntly dissected and the tibial shaft was prepared free of tissue to as great an extent as possible. After reaming the medullary cavity, an intramedullary nail (diameter 8 mm) was inserted via a hole in the anterior tibial plateau. The inserted nail was locked with two proximal and two distal bolts. A 20 mm osteoperiostal segmental defect was then created in the mid-shaft of the tibia with the aid of a thread saw and an oscillating saw.

The defect was filled according to the treatment group. In one group, autologous bone was harvested from the ipsilateral iliac crest and placed into the defect. In the other group, approximately 2–4 g of the hydrated PCA calcium phosphate precursor (type 2 or type 10) was applied by hand to fill the defect. The soft tissues and the skin were closed in layers with resorbable suture material.

The animals received post operative lincomycin/spectinomycin (Vualin Plus®, 5 mg/10 mg per kg per day) for 3 days by intramuscular injection. The animals were kept outside in the meadow as soon as full weight bearing of the operated limb was possible. Animals were sacrificed prior to explanation of the tibiae as follows: As a premedication ketamin (Aescoket®, 500 mg i.m.) and xylazin (Rompun®, 40 mg i.m.) were given. Then 0.5 mg fentanylcitrate (Fentanyl®), 10 mg etomidate (Hypnomidate®), 4 mg pancuronium bromide (Pavulon®), and 1.4 gram potassium chloride were administered intravenously.

Animals receiving the inventive PCA calcium phosphate demonstrated complete healing at three months. The test bones were then dissected from the animal and tested for strength. Preliminary results indicated that the inventive PCA calcium phosphate was resorbed and ossified to produce bone equal to or better than autologous implants in less than three months.

EXAMPLE 30

The purpose of this study was to evaluate resorption, ossification and biocompatibility of two formulations of the inventive PCA calcium phosphate in canine mandibular sites. Prehardened PCA calcium phosphate was implanted in a canine mandibular onlay model which additionally may be used as an augmentation model.

The test article was PCA calcium phosphate in two formulations, corresponding to Types 2 and 10 described in Example 18. The PCA calcium phosphate was pre-hardened in a moist environment at approx. 40° C. immediately prior to implantation. The control implants were 3 mm×4 mm cylinders of silicone and porous hydroxyapatite, respectively.

Two adult female hound-type dogs (20 to 25 kg) were used in the study. Both dogs received two control implants (1 of each) on the right side of the mandible and one each of the Type 2 and Type 10 PCA calcium phosphate formulations on the left (opposite) side.

Implantation was performed under full anesthesia and aseptic surgical conditions. The animals were premedicated with tranquilizers and atropine-type agents and induced with barbiturates. The animal's vital signs (temperature, heart rate, respiratory rate) were monitored before and throughout the procedure. The animals were tested for proper anesthetic depth by toe pinch and corneal stimulus. After obtaining adequate anesthesia, using aseptic technique, an incision was made in the skin over the midlateral ventral surface of the mandible and proximal neck (over the mandible lower edge). The soft tissue was deflected away and the bone was exposed. The periosteum over the outer mandibular surface was elevated and the bone surface was roughened with a burr or drill until it was rough and bloody in a shape to accept the cylindrical implants. The control articles and pre-hardened PCA calcium phosphate were placed into the defects. Two samples per animal per side were onlaid onto each outer mandible surface using this method (two experimental PCA calcium phosphate samples and two controls). The samples were placed about 1 cm to insure that they do not appose each other. The periosteum was closed first using 3.0 vicryl. The soft tissues were then closed in layers with 3-0 vicryl absorbable suture. The skin was closed with simple interrupted sutures of 5-0 nylon. The animals were allowed to heal for scheduled periods of time. One dog was sacrificed at 3 weeks and the other at 3 months and the test sites were removed for histology. All animals were euthanized and identifying marks were collected.

The implantation sites were prepared as undecalcified sections. Sections were evaluated for biointegration, biodegradation, and biocompatibility.

The results were as follows: At all time points excellent biocompatibility was observed. No giant cells and minimal macrophage were observed. There was only minimal reaction layer of only a few cells thickness at the base of the PCA calcium phosphate implants. This is significantly better than was observed for either of the controls.

At three weeks, the majority of the Type 2 material was resorbed. At twelve weeks, the Type 2 was completely resorbed to the surface of the original bone. Additionally the bone in the socket was not fully differentiated.

The Type 10 samples demonstrated osseointegration with new bone ingrowth and cell migration into the implant. The implant itself was approximately 10% resorbed after twelve weeks.

The silicon control implant, which is not resorbable, displayed a mild to moderate foreign body reaction. Voids were unfilled at three weeks, but by twelve weeks were filled with fibrous tissue. The hydroxyapatite control implant showed no signs of resorption or osseointegration within the first twelve weeks.

This experiment confirms the excellent biocompatibility of the inventive PCA calcium phosphate. Additionally, a difference in resorption time between the two PCA formulations was observed, with a prolonged resorption time course for the sample in which the precursors were mixed/ground for a longer period of time (Type B).

The results also point out the slower resorption and ossification properties observed in the non-load bearing mandible implant site as compared to the rapidly ossifying load bearing applications of Example 29. Finally, the results demonstrate the need for slowly resorbing PCAs for proper osseointegration in augmentation plastic surgery.

EXAMPLE 31

This example demonstrates the effect of maintaining the hydrated precursor uncovered at room temperature.

The dry precursor was prepared as described in Example 11(b). The dry precursor was mixed with the indicated amount of water and tested for hardening and injectability through a 16 gauge needle after standing uncovered at room temperature for various time periods. The results are reported in Table 10.

Table 10

Paste Injectability after Standing at Room Temperature

| sample wt (g) | water added (mL) | mixing time (s) | standing time (min) | room temp. (° C.) | injectability for 16 gauge needle | hardening; 30 min/37° C. |
| --- | --- | --- | --- | --- | --- | --- |
| 1 | 0.8 | 20 | 10 | 25 | v. good | v. good |
| 1 | 0.8 | 20 | 20 | 24 | v. good | v. good |
| 1 | 0.8 | 20 | 30 | 25 | v. good | v. good |
| 1 | 0.8 | 20 | 40 | 25 | good | v. good |
| 1 | 0.8 | 20 | 50 | 24 | poor | v. good |
| 5 | 4.2 | 40 | 10 | 24 | v. good | v. good |
| 5 | 4.2 | 40 | 20 | 25 | v. good | v. good |

-continued

| sample wt (g) | water added (mL) | mixing time (s) | standing time (min) | room temp. (° C.) | injectability for 16 gauge needle | hardening; 30 min/37° C. |
|---|---|---|---|---|---|---|
| 5 | 4.2 | 40 | 30 | 25 | good | v. good |
| 5 | 4.2 | 40 | 40 | 25 | poor | v. good |

These results demonstrate that a one gram sample may be stable as an injectable paste at ambient conditions for up to 45 minutes and that a 5 gram sample may be stable as an injectable paste for up to 30 minutes at ambient conditions (in air, 25° C.).

OTHER EMBODIMENTS

It will be understood that the foregoing is merely descriptive of certain preferred embodiments of the invention and is not intended to be limiting thereof. The following claims cover all of the generic and specific features of the invention herein described in the text and accompanying drawings.

What is claimed is:

1. A formable paste, suitable for use as a bone substitution material, comprising a mixture of:
   (a) a powder component, comprising:
      (i) an amorphous calcium phosphate having a Ca/P molar ratio between 1.1 and 1.55, wherein said amorphous calcium phosphate is present in an amount greater than 20 wt % of said powder component, and
      (ii) a second, crystalline calcium phosphate; and
   (b) a physiologically acceptable fluid in an amount to provide a paste having a formable or injectable consistency,
   wherein the amorphous calcium phosphate and the second calcium phosphate, in combination, have a stoichiometry that permits formation of a calcium-deficient, poorly crystalline apatitic (PCA) calcium phosphate.

2. The paste of claim 1, wherein the paste self-hardens at temperatures at or greater than ambient.

3. The paste of claim 1, wherein the amorphous calcium phosphate and the second calcium phosphate are present in a ratio of about 1:1.

4. The paste of claim 1, wherein the second calcium phosphate is selected from the group consisting of dicalcium phosphate dihydrate (DCPD), monetite, calcium metaphosphate, heptacalcium phosphate, calcium pyrophosphates and tricalcium phosphates, hydroxyapatite, and octacalcium phosphate.

5. The paste of claim 1 or 2, further comprising an additional material selected to change a physical parameter of the paste and/or hardened PCA calcium phosphate product consisting of strength, resorption time, adherence, injectability, frictional characteristics, release kinetics, tensile strength, hardness, fracture toughness, elasticity, imaging capability, flow properties and setting times.

6. The paste of claim 1, further comprising a therapeutic substance.

7. The paste of claim 1, wherein the physiologically acceptable fluid is selected from the group consisting of water, saline, buffer solutions, serum and tissue culture medium.

8. The paste of claim 1, wherein the physiologically acceptable fluid is a pH-buffered solution having a pH in the range of 5.0 to 8.0.

9. The paste of claim 8, wherein the pH-buffered solution has a pH in the range of 5.5 to 7.4.

10. The paste of claim 6, wherein said therapeutic substance is selected from the group consisting of growth factors, antibiotics, anti-cancer agents, and analgesics.

11. The paste of claim 1, further comprising a crystallization inhibitor selected from the group consisting of carbonates, pyrophosphate, and magnesium.

12. The paste of claim 1, wherein the paste remains formable for at least one hour at temperatures less than or equal to ambient but hardens at body temperature.

* * * * *